United States Patent [19]

Linker et al.

[11] Patent Number: 5,476,946
[45] Date of Patent: Dec. 19, 1995

[54] 1-ARYLTRIAZOLIN(ETHI)ONES

[75] Inventors: Karl-Heinz Linker; Kurt Findeisen, both of Leverkusen; Wilhelm Haas, Pulheim; Otto Schallner, Monheim; Markus Dollinger, Leichlingen; Hans-Joachim Santel, Leverkusen, all of Germany

[73] Assignee: Bayer Aktiengesellschaft, Leverkusen, Germany

[21] Appl. No.: 190,813

[22] Filed: Feb. 2, 1994

[30] Foreign Application Priority Data

Feb. 9, 1993 [DE] Germany ............ 43 03 676.7

[51] Int. Cl.⁶ .............. A01N 43/653; A01N 57/32; C07D 249/12; C07F 9/02
[52] U.S. Cl. .............. 504/273; 504/197; 548/112; 548/263.8
[58] Field of Search .............. 504/197, 273; 548/112, 263.8

[56] References Cited

U.S. PATENT DOCUMENTS

| | | | |
|---|---|---|---|
| 4,906,284 | 3/1990 | Theodoridis | 548/263.2 |
| 5,244,803 | 9/1993 | Kawamura | 504/216 |
| 5,314,889 | 5/1994 | Boigegrain | 514/253 |

FOREIGN PATENT DOCUMENTS

| | | |
|---|---|---|
| 0055105 | 6/1982 | European Pat. Off. |
| 2910330 | 10/1980 | Germany. |
| WO8604481 | 8/1986 | WIPO. |
| 9402472 | 2/1994 | WIPO. |

OTHER PUBLICATIONS

J. Heterocyclic Chem., vol. 27, pp. 575–577, 3–4/90; "Picryl Derivatives of 5–Nitro–2,4–dihydro–3H–1,2, 4–triazol–3–one", M. D. Coburn et al.
Chem. Ber., vol. 102, pp. 755–766, 1969; "Über 1.2.4–Triazole, XVII²⁾ . . . ", C. F. Kröger et al.

Primary Examiner—Patricia L. Morris
Attorney, Agent, or Firm—Sprung Horn Kramer & Woods

[57] ABSTRACT

The invention relates to new 1-aryltriazolin(ethi)ones of the general formula (I)

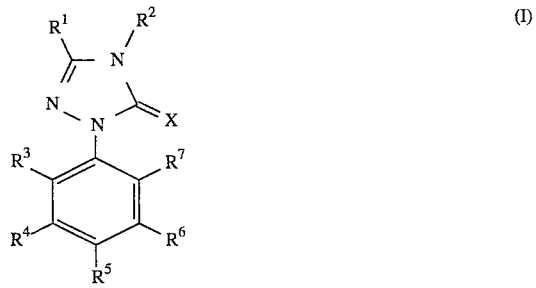

in which $R^1$ represents nitro or represents a radical —$NR^8R^9$, $R^2$ represents hydrogen, amino or cyano, or represents one of the radicals —$R^{10}$, —O—$R^{10}$, —S—$R^{10}$, —$NR^{10}R^{11}$, —$N(R^{11})$—CO—$R^{10}$ or —N=$CR^{10}R^{11}$, $R^3$, $R^6$ and $R^7$ independently of one another each represent hydrogen, halogen or nitro, $R^4$ represents hydrogen, halogen, cyano or nitro, or represents one of the radicals —$R^{12}$, —O—$R^{12}$, —S—$R^{12}$, —S(O)—$R^{12}$, —$SO_2$—$R^{12}$, —SO—$OR^{12}$, —SO—$NR^{11}R^{12}$, —CO—$OR^{12}$, —CO—$NR^{11}R^{12}$, —O—$SO_2$—$R^{12}$, —$N(R^{11})$—$SO_2$—$R^{12}$, —$NR^{11}R^{12}$, —NH—P(O)($R^{11}$)($OR^{12}$) or —NH—P(O)($OR^{11}$)($OR^{12}$), $R^5$ represents nitro, cyano, halogen or halogenoalkyl, and X represents oxygen or sulphur, where $R^8$ and $R^9$ independently of one another each represent hydrogen or represent in each case optionally substituted alkyl, alkenyl, alkinyl, alkoxy, cycloalkyl, aryl or heterocyclyl, or represent, together with the nitrogen atom to which they are attached, an optionally substituted heterocycle, $R^{10}$ represents in each case optionally substituted alkyl, alkenyl, alkinyl, cycloalkyl, aryl, arylalkyl or heterocyclyl, $R^{11}$ represents hydrogen or represents in each case optionally substituted alkyl, alkenyl, alkinyl, cycloalkyl, arylalkyl or aryl, and $R^{12}$ represents hydrogen or represents in each case optionally substituted alkyl, alkenyl, alkinyl, cycloalkyl, aryl or heterocyclyl, to a number of processes for their preparation, to a number of new intermediates, and to their use as herbicides.

8 Claims, No Drawings

1-ARYLTRIAZOLIN(ETHI)ONES

The invention relates to new 1-aryltriazolin(ethi)ones, to a number of processes for their preparation, to a number of new intermediates, and to their use as herbicides.

It is known that certain 1-aryltriazolin(ethi)ones, such as, for example, the compound 3-methyl-4-proparyl 1-(2,5-difluoro-4-cyano-phenyl)-1,2,4-triazolin-5-one, possess herbicidal properties (cf. e.g. DE 38 39 480).

The herbicidal activity of these already known compounds against problem weeds is, however, just like their tolerance by important crop plants, not entirely satisfactory in all areas of application.

New 1-aryltriazolin (ethi) ones have been found, of the general formula (I),

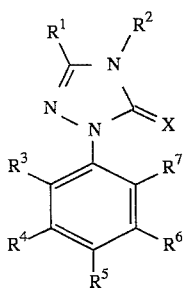

(I)

in which $R^1$ represents nitro or represents a radical —$NR^6R^9$, $R^2$ represents hydrogen, amino or cyano, or represents one of the radicals —$R^{10}$, —O—$R^{10}$, —S—$R^{10}$, —$NR^{10}R^{11}$, —N(R)—CO—$R^{10}$ or —N=$CR^{10}R^{11}$, $R^3$, $R^6$ and $R^7$ independently of one another each represent hydrogen, halogen or nitro, $R^4$ represents hydrogen, halogen, cyano or nitro, or represents one of the radicals —$R^{12}$, —O—$R^{12}$, —S—$R^{12}$, —S(O)—$R^{12}$, —$SO_2$—$R^{12}$, —$SO_2$—$OR^{12}$, —SO—$NR^{11}R^{12}$, —CO—$OR^{12}$, —CO—$NR^{11}R^{12}$, —O—$SO_2$—$R^{12}$, —N($R^{11}$)—SO—$R^{12}$, —$NR^{11}R^{12}$, —NH—P(O)($R^{11}$)($OR^{12}$) or —NH—P(O)($OR^{11}$)($OR^{12}$), $R^5$ represents nitro, cyano, halogen or halogenoalkyl and X represents oxygen or sulphur, where $R^6$ and $R^9$ independently of one another each represent hydrogen or represent in each case optionally substituted alkyl, alkenyl, alkinyl, alkoxy, cycloalkyl, aryl or heterocyclyl, or represent, together with the nitrogen atom to which they are attached, an optionally substituted heterocycle, $R^{10}$ represents in each case optionally substituted alkyl, alkenyl, alkinyl, cycloalkyl, aryl, arylalkyl or heterocyclyl, $R^{11}$ represents hydrogen or represents in each case optionally substituted alkyl, alkenyl, alkinyl, cycloalkyl, arylalkyl or aryl, and $R^{12}$ represents hydrogen or represents in each case optionally substituted alkyl, alkenyl, alkinyl, cycloalkyl, aryl or heterocyclyl.

The compounds of the formula (I) may possibly be present, depending on the nature of the substituents, as geometric and/or optical isomers or isomer mixtures of varying composition. Both the pure isomers and the isomer mixtures are claimed in accordance with the invention.

It has furthermore been found that the new 1-aryltriazolin(ethi)ones of the general formula (I),

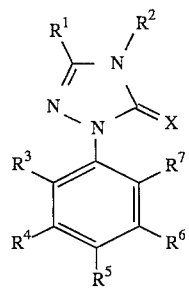

(I)

in which $R^1$ represents nitro or represents a radical —$NR^6R^9$, $R^{12}$ represents hydrogen, amino or cyano, or represents one of the radicals —$R^{10}$, —O—$R^{10}$, —S—$R^{10}$, —$NR^{10}R^{11}$, —N(R)—CO—$R^{10}$ or —N=$CR^{10}R^{11}$, $R^3$, $R^6$ and $R^7$ independently of one another each represent hydrogen, halogen or nitro, $R^4$ represents hydrogen, halogen, cyano or nitro, or represents one of the radicals —$R^{12}$, —O—$R^{12}$, —S—$R^{12}$, —S(O)—$R^{12}$, —SO—$R^{12}$, —SO—$OR^{12}$, —$SO_2$—$NR^{11}R^{12}$, —CO—$OR^{12}$, —CO—$NR^{11}R^{12}$, —O—$SO_2$—$R^{12}$, —N($R^{11}$)—$SO_2$—$R^{12}$, —$NR^{11}R^{12}$, —NH—P(O)($R^{11}$)($OR^{12}$) or —NH—P(O)($OR^{11}$)($OR^{12}$), $R^5$ represents nitro, cyano, halogen or halogenoalkyl, and X represents oxygen or sulphur, where $R^8$ and $R^9$ independently of one another each represent hydrogen or represent in each case optionally substituted alkyl, alkenyl, alkinyl, alkoxy, cycloalkyl, aryl or heterocyclyl, or represent, together with the nitrogen atom to which they are attached, an optionally substituted heterocycle, $R^{10}$ represents in each case optionally substituted alkyl, alkenyl, alkinyl, cycloalkyl, aryl, arylalkyl or heterocyclyl, $R^{11}$ represents hydrogen or represents in each case optionally substituted alkyl, alkenyl, alkinyl, cycloalkyl, arylalkyl or aryl, and $R^{12}$ represents hydrogen or represents in each case optionally substituted alkyl, alkenyl, alkinyl, cycloalkyl, aryl or heterocyclyl, are obtained if a) 1H-triazolinones of the formula (II),

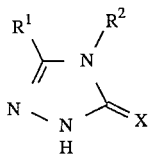

(II)

in which $R^{11}$, $R^{12}$ and X have the definitions given above, are reacted with halogenobenzene derivatives of the formula (III),

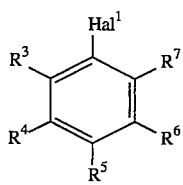

(III)

in which

R$^3$, R$^4$, R$^5$, R$^6$ and R$^7$ have the definitions given above and

Hal$^1$ represents halogen, optionally in the presence of a diluent and optionally in the presence of a reaction auxiliary, or if b) substituted triazolinones of the formula (Ia),

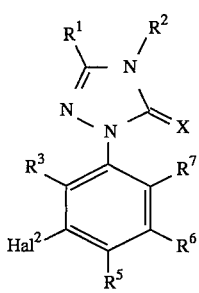

(Ia)

in which

R$^1$, R$^2$, R$^3$, R$^5$, R$^6$, R$^7$ and X have the definitions given above and Hal$^2$ represents halogen, are reacted with nucleophiles of the formula (IV),

 (IV)

in which

R$^{13}$ represents a radical of the formula —O—R$^{12}$, —S—R$^{12}$ or —NR$^{11}$R$^{12}$, where R$^{11}$ and R$^{12}$ have the definitions given above, optionally in the presence of a diluent and optionally in the presence of a reaction auxiliary, or if c) substituted triazolinones of the formula (Ib),

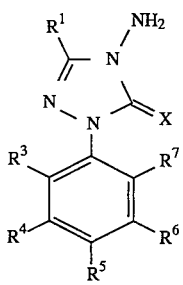

(Ib)

in which

R$^1$, R$^3$, R$^4$, R$^5$, R$^6$, R$^7$ and X have the definitions given above, are reacted with sodium nitrite in the presence of an acid and optionally in the presence of a diluent, or if d) substituted triazolinones of the formula (Ic),

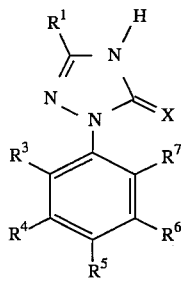

(Ic)

in which

R$^1$, R$^3$, R$^4$, R$^5$, R$^6$, R$^7$ and X have the definitions given above, are reacted with alkylating agents of the formula in which (V),

 (V)

in which

R$^{2-1}$ represents in each case optionally substituted alkyl, alkenyl, alkinyl or cycloalkyl, and E$^1$ represents an electron-attracting leaving group, optionally in the presence of a diluent and optionally in the presence of a reaction auxiliary, or if d) chloro-formamidinium hydrochlorides of the formula (VI),

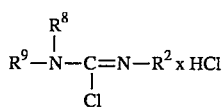

(VI)

in which

R$^2$, R$^8$ and R$^9$ have the definitions given above, are first reacted in a first stage with arylhydrazines of the formula (VII),

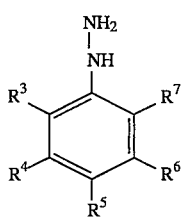

(VII)

in which

R$^3$, R$^4$, R$^5$, R$^6$ and R$^7$ have the definitions given above, optionally in the presence of a diluent, and in a subsequent second stage the intermediates which can be obtained in this manner, of the formula (VIII),

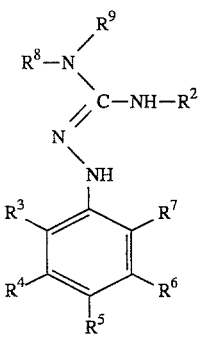

in which

R², R³, R⁴, R⁵, R⁶, R⁷, R⁸ and R⁹ have the definitions given above, are cyclized with phosgene or thiophosgene, optionally in the presence of a diluent and optionally in the presence of a reaction auxiliary.

Finally, it has been found that the new 1-aryltriazolin(ethi)ones of the general formula (I) possess herbicidal properties.

Surprisingly, the 1-aryltriazolin(ethi)ones of the general formula (I) according to the invention display a considerably improved herbicidal activity against problem weeds with a comparable tolerance by crop plants in comparison to the substituted triazolinones known from the prior art, such as, for example, the compound 3-methyl-4-propargyl-1-(2,5-difluoro-4-cyano-phenyl)-1,2,4-triazolin-5-one, which are closely related compounds in terms of their chemistry and their action.

A general definition of the 1-aryltriazolin(ethi)ones according to the invention is given by the formula (I). Preferred compounds of the formula (I) are those in which $R^1$ represents nitro or represents a radical —NR⁸R⁹, $R^2$ represents hydrogen, amino or cyano, or represents one of the radicals —R¹⁰, —O—R¹⁰, —S—R¹⁰, —NR¹⁰R¹¹, —N(R)—CO—R¹⁰ or —N=CR¹⁰R¹¹, $R^3$, $R^6$ and $R^7$ independently of one another each represent hydrogen, fluorine, chlorine, bromine, iodine or nitro, $R^4$ represents hydrogen, fluorine, chlorine, bromine, iodine, cyano or nitro, or represents one of the radicals —R¹², —O—R¹², —S—R¹², —S(O)—R¹², —SO—R¹², —SO₂—OR¹², —SO₂—NR¹¹R¹², —CO—OR¹², —CO—NR¹¹R¹², —O—SO₂—R¹², —N(R¹¹)—SO₂—R¹², —NR¹¹R¹², —NH—P(O)(R¹¹)(OR¹²) or —NH—P(O)(OR¹¹) (OR¹²), $R^5$ represents nitro, cyano, fluorine, chlorine, bromine, iodine, or represents straight-chain or branched halogenoalkyl having 1 to 6 carbon atoms and 1 to 13 identical or different halogen atoms, and X represents oxygen or sulphur, where $R^8$ and $R^9$ independently of one another in each case represent hydrogen;

$R^8$ and $R^5$ furthermore represent straight-chain or branched alkyl or alkoxy having in each case 1 to 14 carbon atoms, which are in each case optionally substituted once or more than once by identical or different substituents, possible substituents in each case being: halogen, in particular fluorine, chlorine, bromine and/or iodine, cyano, carboxyl, carbamoyl, in each case straight-chain or branched alkoxy, alkoxyalkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 8 carbon atoms in the individual alkyl moieties, or heterocyclyl, the heterocyclyl radical being a five- to seven-membered, optionally benzo-fused, saturated or unsaturated heterocycle having 1 to 3 identical or different heteroatoms in particular nitrogen, oxygen and/or sulphur;

$R^8$ and $R^9$ furthermore represent alkenyl or alkinyl having in each case 2 to 8 carbon atoms, which are in each case optionally substituted once or more than once by identical or different halogens—in particular fluorine, chlorine, bromine and/or iodine;

$R^8$ and $R^9$ furthermore represent cycloalkyl having 3 to 7 carbon atoms which is optionally substituted once or more than once by identical or different halogens— in particular fluorine, chlorine, bromine and/or iodine— and/or by straight-chain or branched alkyl having 1 to 4 carbon atoms;

$R^8$ and $R^9$ furthermore represent arylalkyl or aryl having in each case 6 to 10 carbon atoms in the aryl moiety and optionally 1 to 4 carbon atoms in the straight-chain or branched alkyl moiety, which are in each case optionally substituted in the aryl moiety once or more than once by identical or different substituents, or represent a saturated or unsaturated, five- to seven-membered heterocyclyl radical having 1 to 3 identical or different heteroatoms—in particular nitrogen, oxygen and/or sulphur—which is optionally substituted once or more than once by identical or different substituents and/or is benzo-fused, possible substituents of the aryl or heterocyclyl in each case being: halogen, cyano, nitro, amino, N-acetylamino, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxycarbonyl or alkoximinoalkyl having in each case 1 to 6 carbon atoms in the individual alkyl moieties, and phenyl which is optionally substituted once or more than once by identical or different substituents comprising halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms;

$R^8$ and $R^9$ furthermore represent, together with the nitrogen atom to which they are attached, a saturated or unsaturated, five- to seven-membered heterocyclyl radical having 1 to 3 identical or different heteroatoms—in particular nitrogen, oxygen and/or sulphur— which is optionally substituted once or more than once by identical or different substituents and/or is benzo-fused, possible substituents of heterocyclyl being: halogen, cyano, nitro, amino, N-acetylamino, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxycarbonyl or alkoximinoalkyl having in each case 1 to 6 carbon atoms in the individual alkyl moieties, and phenyl which is optionally substituted once or more than once by identical or different substituents comprising halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms;

$R^{10}$ represents straight-chain or branched alkyl having 1 to 14 carbon atoms which is optionally substituted once or more than once by identical or different substituents, possible substituents being: halogen, in particular fluorine, chlorine, bromine and/or iodine, cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 8 carbon atoms in the individual alkyl moieties, or heterocyclyl, the heterocyclyl radical being a five- to seven-membered, optionally benzo-fused, saturated or unsaturated heterocycle having 1 to 3 identical or different heteroatoms in particular nitrogen, oxygen and/or sulphur;

$R^{10}$ furthermore represents alkenyl or alkinyl having in each case 2 to 8 carbon atoms, which are in each case optionally substituted once or more than once by identical or different halogens—in particular fluorine, chlorine, bromine and/or iodine;

$R^{10}$ furthermore represents cycloalkyl having 3 to 7 carbon atoms which is optionally substituted once or more than once by identical or different substituents comprising halogen—in particular fluorine, chlorine, bromine and/or iodine—and/or straight-chain or branched alkyl having 1 to 4 carbon atoms;

$R^{10}$ furthermore represents arylalkyl or aryl having in each case 6 to 10 carbon atoms in the aryl moiety and optionally 1 to 4 carbon atoms in the straight-chain or branched alkyl moiety, which are in each case optionally substituted in the aryl moiety once or more than once by identical or different substituents, or represents a saturated or unsaturated, five- to seven-membered heterocyclyl radical having 1 to 3 identical or different heteroatoms—in particular nitrogen, oxygen and/or sulphur—which is optionally substituted once or more than once by identical or different substituents and/or is benzo-fused, possible substituents of aryl and/or heterocyclyl being: halogen, cyano, nitro, amino, N-acetylamino, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxycarbonyl or alkoximinoalkyl having in each case 1 to 6 carbon atoms in the individual alkyl moieties, and phenyl which is optionally substituted once or more than once by identical or different substituents comprising halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms;

$R^{11}$ represents hydrogen;

$R^{11}$ furthermore represents straight-chain or branched alkyl having 1 to 14 carbon atoms which is optionally substituted once or more than once by identical or different substituents, possible substituents being: halogen, in particular fluorine, chlorine, bromine and/or iodine, cyano, carboxyl, carbamoyl, in each case straight-chain or branched alkoxy, alkoxy alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 8 carbon atoms in the individual alkyl moieties, or heterocyclyl, the heterocyclyl radical being a five- to seven-membered, optionally benzo-fused, saturated or unsaturated heterocycle having 1 to 3 identical or different heteroatoms in particular nitrogen, oxygen and/or sulphur;

$R^{11}$ furthermore represents alkenyl or alkinyl having in each case 2 to 8 carbon atoms, which are in each case optionally substituted once or more than once by identical or different halogens—in particular fluorine, chlorine, bromine and/or iodine;

$R^{11}$ furthermore represents cycloalkyl having 3 to 7 carbon atoms which is optionally substituted once or more than once by identical or different substituents comprising halogen—in particular fluorine, chlorine, bromine and/or iodine—and/or straight-chain or branched alkyl having 1 to 4 carbon atoms;

$R^{11}$ furthermore represents arylalkyl or aryl having in each case 6 to 10 carbon atoms in the aryl moiety and optionally 1 to 4 carbon atoms in the straight chain or branched alkyl moiety, which are in each case optionally substituted in the aryl moiety once or more than once by identical or different substituents, possible substituents of aryl in each case being:

halogen, cyano, nitro, amino, N-acetylamino, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxycarbonyl or alkoximinoalkyl having in each case 1 to 6 carbon atoms in the individual alkyl moieties, and phenyl which is optionally substituted once or more than once by identical or different substituents comprising halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms;

$R^{12}$ represents hydrogen;

$R^{12}$ furthermore represents straight-chain or branched alkyl having 1 to 14 carbon atoms which is optionally substituted once or more than once by identical or different substituents, possible substituents being:

halogen, in particular fluorine, chlorine, bromine and/or iodine, cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 8 carbon atoms in the individual alkyl moieties, or heterocyclyl, the heterocyclyl radical being a five- to seven-membered, optionally benzo-fused, saturated or unsaturated heterocycle having 1 to 3 identical or different heteroatoms— in particular nitrogen, oxygen and/or sulphur;

$R^{12}$ furthermore represents alkenyl or alkinyl having in each case 2 to 8 carbon atoms, which are in each case optionally substituted once or more than once by identical or different halogens—in particular fluorine, chlorine, bromine and/or iodine;

$R^{12}$ furthermore represents cycloalkyl having 3 to 7 carbon atoms which is optionally substituted once or more than once by identical or different substituents comprising halogen—in particular fluorine, chlorine, bromine and/or iodine—and/or straight-chain or branched alkyl having 1 to 4 carbon atoms;

$R^{12}$ furthermore represents arylalkyl or aryl having in each case 6 to 10 carbon atoms in the aryl moiety and optionally 1 to 4 carbon atoms in the straight-chain or branched alkyl moiety, which are in each case optionally substituted in the aryl moiety once or more than once by identical or different substituents, or represents a saturated or unsaturated, five- to seven-membered heterocyclyl radical having 1 to 3 identical or different heteroatoms—in particular nitrogen, oxygen and/or sulphur—which is optionally substituted once or more than once by identical or different substituents and/or is benzo-fused, possible substituents of aryl and/or heterocyclyl being in each case:

halogen, cyano, nitro, amino, N-acetylamino, in each case straight-chain or branched alkyl, alkoxy, alkylthio, alkylsulphinyl or alkylsulphonyl having in each case 1 to 6 carbon atoms, in each case straight-chain or branched halogenoalkyl, halogenoalkoxy, halogenoalkylthio, halogenoalkylsulphinyl or halogenoalkylsulphonyl having in each case 1 to 6 carbon atoms and 1 to 13 identical or different halogen atoms, in each case straight-chain or branched alkoxycarbonyl or alkoximinoalkyl having in each case 1 to 6 carbon atoms in the individual alkyl moieties, and phenyl which is optionally substituted once or more than once by identical or different substituents comprising halogen and/or straight-chain or branched alkyl or alkoxy having in each case 1 to 6 carbon atoms and/or straight-chain or branched halogenoalkyl or halogenoalkoxy having in each case 1 to 6 carbon atoms and 1 to 13 identical or different halogen atoms.

Particularly preferred compounds of the formula (I) are those in which $R^1$ represents nitro or represents a radical —$NR^8R^9$, $R^2$ represents hydrogen, amino or cyano, or represents one of the radicals —$R^{10}$, —O—$R^{10}$, —S —$R^{10}$, —$NR^{10}R^{11}$, —$N(R^{11})$—CO—$R^{10}$ or —$N=CR^{10}R^{11}$, $R^3$, $R^6$ and $R^7$ independently of one another each represent hydrogen, fluorine chlorine, bromine or nitro, $R^4$ represents hydrogen, fluorine chlorine, bromine, cyano or nitro, or represents one of the radicals —$R^{12}$, —O—$R^{12}$, —S—$R^{12}$, —S(O)—$R^{12}$, —$SO_2$—$R^{12}$, —$SO_2$—$OR^{12}$, —$SO_2$—$NR^{11}R^{12}$, —CO—$OR^{12}$, —CO—$NR^{11}R^{12}$, —O—$SO_2$—$R^{12}$, —$N(R^{11})$—$SO_2$—$R^{12}$, —$NR^{11}R^{12}$, —NH—P(O)($R^{11}$)($OR^{12}$) or —NH—P(O)($OR^{11}$)($OR^{12}$), $R^5$ represents nitro, cyano, fluorine, chlorine, bromine or represents straight-chain or branched halogenoalkyl having 1 to 4 carbon atoms and 1 to 9 identical or different halogen atoms, and X represents oxygen or sulphur, where $R^8$ and $R^9$ independently of one another each represent hydrogen;

$R^8$ and $R^9$ furthermore represent straight-chain or branched alkyl or alkoxy having in each case 1 to 12 carbon atoms, which are in each case optionally substituted once or more than once by identical or different substituents, possible substituents in each case being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 6 carbon atoms in the individual alkyl moieties, or heterocyclyl, the heterocyclyl radical being a five- to seven-membered, optionally benzo-fused- saturated or unsaturated heterocycle having 1 to 3 identical or different heteroatoms—in particular nitrogen, oxygen and/or sulphur;

$R^8$ and $R^9$ furthermore represent in each case straight-chain or branched halogenoalkyl or halogenoalkoxy having in each case 1 to 6 carbon atoms and 1 to 13 identical or different halogen atoms—in particular fluorine, chlorine and/or bromine;

$R^8$ and $R^9$ furthermore represent alkenyl or alkinyl having in each case 2 to 8 carbon atoms, which are in each case optionally substituted once to five times by identical or different halogens—in particular fluorine, chlorine and/or bromine;

$R^8$ and $R^9$ furthermore represent cycloalkyl having 3 to 6 carbon atoms which is optionally substituted once to five times by identical or different substituents comprising halogen—in particular fluorine, chlorine and/or bromine—and/or straight-chain or branched alkyl having 1 to 3 carbon atoms;

$R^8$ and $R^9$ furthermore represent phenylalkyl or phenyl having optionally 1 to 4 carbon atoms in the straight-chain or branched alkyl moiety, which are in each case optionally substituted in the phenyl moiety once to five times by identical or different substituents, or represent a saturated or unsaturated, five- to seven-membered heterocyclyl radical having 1 to 3 identical or different heteroatoms—in particular nitrogen, oxygen and/or sulphur—which is optionally substituted once to three times by identical or different substituents and/or is benzo-fused, possible substituents of phenyl and/or heterocyclyl in each case being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl moieties, and phenyl which is optionally substituted once to five times by identical or different substituents comprising fluorine, chlorine, bromine and/or straight-chain or branched alkyl or alkoxy having in each case 1 to 4 carbon atoms and/or straight-chain or branched halogenoalkyl or halogenoalkoxy having in each case 1 to 4 carbon atoms and 1 to 9 identical or different halogen atoms;

$R^8$ and $R^9$ furthermore represent, together with the nitrogen atom to which they are attached, a saturated or unsaturated—five- to seven-membered heterocyclyl radical having 1 to 3 identical or different heteroatoms—in particular nitrogen, oxygen and/or sulphur—which is optionally substituted once to three times by identical or different substituents and/or is benzo-fused, possible substituents of heterocyclyl being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl moieties, and phenyl which is optionally substituted once to five times by identical or different substituents comprising fluorine, chlorine, bromine and/or straight-chain or branched alkyl or alkoxy having in each case 1 to 4 carbon atoms and/or straight-chain or branched halogenoalkyl or halogenoalkoxy having in each case 1 to 4 carbon atoms and 1 to 9 identical or different halogen atoms;

$R^{10}$ represents straight-chain or branched alkyl having 1 to 12 carbon atoms which is optionally substituted once or twice by identical or different substituents, possible substituents being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 6 carbon atoms in the individual alkyl moieties, or heterocyclyl, the heterocyclyl radical being a five- to seven-membered—optionally benzo-fused, saturated or unsaturated heterocycle having 1 to 3 identical or different heteroatoms—in particular nitrogen, oxygen and/or sulphur;

$R^{10}$ furthermore represents straight-chain or branched halogenoalkyl having 1 to 6 carbon atoms and 1 to 13 identical or different halogen atoms—in particular fluorine, chlorine and/or bromine, $R^{10}$ furthermore represents alkenyl or alkinyl having in each case 2 to 6 carbon atoms, which are in each case optionally substituted once to three times by identical or different halogens—in particular fluorine, chlorine and/or bromine;

$R^{10}$ furthermore represents cycloalkyl having 3 to 7 carbon atoms which is optionally substituted once to three times by identical or different substituents comprising halogen—in particular fluorine, chlorine and/or bromine—and/or straight-chain or branched alkyl having 1 to 3 carbon atoms;

$R^{10}$ furthermore represents phenylalkyl or phenol having optionally 1 to 3 carbon atoms in the straight-chain or branched alkyl moiety, which are in each case optionally substituted in the phenyl moiety once to five times by identical or different substituents, or represents a saturated or unsaturated, five- to seven-membered heterocyclyl radical having 1 to 3 identical or different heteroatoms—in particular nitrogen, oxygen and/or sulphur—which is optionally substituted once to three times by identical or different substituents and/or is benzo-fused, possible substituents of phenyl and/or heterocyclyl in each case being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl moieties, and phenyl which is optionally substituted once to five times by identical or different substituents comprising fluorine, chlorine, bromine and/or straight-chain or branched alkyl or alkoxy having in each case 1 to 4 carbon atoms and/or straight-chain or branched halogenoalkyl or halogenoalkoxy having in each case 1 to 4 carbon atoms and 1 to 9 identical or different halogen atoms;

$R^{11}$ represents hydrogen; represents straight-chain or branched alkyl having 1 to 12 carbon atoms which is optionally substituted once or twice by identical or different substituents, possible substituents being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 6 carbon atoms in the individual alkyl moieties, or heterocyclyl, the heterocyclyl radical being a five- to seven-membered—optionally benzo-fused, saturated or unsaturated heterocycle having 1 to 3 identical or different heteroatoms—in particular nitrogen, oxygen and/or sulphur;

$R^{11}$ furthermore represents straight-chain or branched halogenoalkyl having 1 to 6 carbon atoms and 1 to 13 identical or different halogen atoms—in particular fluorine, chlorine and/or bromine, $R^{12}$ furthermore represents alkenyl or alkinyl having in each case 2 to 6 carbon atoms, which are in each case optionally substituted once to three times by identical or different halogens—in particular fluorine, chlorine and/or bromine;

$R^{11}$ furthermore represents cycloalkyl having 3 to 7 carbon atoms which is optionally substituted once to three times by identical or different substituents comprising halogen—in particular fluorine, chlorine and/or bromine—and/or straight-chain or branched alkyl having 1 to 3 carbon atoms;

$R^{11}$ furthermore represents phenylalkyl or phenyl having optionally 1 to 3 carbon atoms in the straight-chain or branched alkyl moiety, which are in each case optionally substituted in the phenyl moiety once to five times by identical or different substituents, possible substituents of phenyl in each case being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 4 carbon atoms, in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl moieties, and phenyl which is optionally substituted once to five times by identical or different substituents comprising fluorine, chlorine, bromine and/or straight-chain or branched alkyl or alkoxy having in each case 1 to 4 carbon atoms and/or straight-chain or branched halogenoalkyl or halogenoalkoxy having in each case 1 to 4 carbon atoms and 1 to 9 identical or different halogen atoms;

$R^{12}$ represents hydrogen;

$R^{12}$ represents straight-chain or branched alkyl having 1 to 12 carbon atoms which is optionally substituted once or twice by identical or different substituents, possible substituents being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 6 carbon atoms in the individual alkyl moieties, or heterocyclyl, the heterocyclyl radical being a five- to seven-membered, optionally benzo-fused, saturated or unsaturated heterocycle having 1 to 3 identical or different heteroatoms—in particular nitrogen, oxygen and/or sulphur;

$R^{12}$ furthermore represents straight-chain or branched halogenoalkyl having 1 to 6 carbon atoms and 1 to 13 identical or different halogen atoms—in particular fluorine, chlorine and/or bromine, $R^{12}$ furthermore represents alkenyl or alkinyl having in each case 2 to 6 carbon atoms, which are in each case optionally substituted once to three times by identical or different halogens—in particular fluorine, chlorine and/or bromine;

$R^{12}$ furthermore represents cycloalkyl having 3 to 7 carbon atoms which is optionally substituted once to three times by identical or different substituents comprising halogen—in particular fluorine, chlorine and/or bromine—and/or straight-chain or branched alkyl having 1 to 3 carbon atoms;

$R^{12}$ furthermore represents phenylalkyl or phenyl having optionally 1 to 3 carbon atoms in the straight-chain or branched alkyl moiety, which are in each case optionally substituted in the phenyl moiety once to five times by identical or different substituents, or represents a saturated or unsaturated, five- to seven-membered heterocyclyl radical having 1 to 3 identical or different heteroatoms—in particular nitrogen, oxygen and/or sulphur—which is optionally substituted once to three times by identical or different substituents and/or is benzo-fused, possible substituents of phenyl and/or heterocyclyl being in each case:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 4 carbon atoms in each case straight-chain or branched halogenoalkyl, halogenoalkoxy, halogenoalkylthio, halogenoalkylsulphinyl or halogenoalkylsulphonyl having in each case 1 to 4 carbon atoms and 1 to 9 identical or different halogen atoms, in each case straight-chain or branched alkoxycarbonyl or alkoximinoalkyl having in each case 1 to 4 carbon atoms in the individual alkyl moieties, and phenyl which is optionally substituted once to five times by identical or different substituents comprising fluorine, chlorine, bromine and/or straight-chain or branched alkyl or alkoxy having in each case 1 to 4 carbon atoms and/or straight-chain or branched halogenoalkyl or halogenoalkoxy having in each case 1 to 4 carbon atoms and 1 to 9 identical or different halogen atoms.

Very particularly preferred compounds of the formula (I) are those in which $R^1$ represents nitro or represents a radical —$NR^8R^9$, $R^2$ represents hydrogen, amino or cyano, or represents one of the radicals —$R^{10}$, —O—$R^{10}$, —S—$R^{10}$, —$NR^{10}R^{11}$, —N($R^{11}$)—CO—$R^{10}$ or —N=$CR^{10}R^{11}$, $R^3$, $R^6$ and $R^7$ independently of one another each represent hydrogen, fluorine chlorine bromine or nitro, $R^4$ represents hydrogen, fluorine, chlorine, bromine, cyano or nitro, or represents one of the radicals —$R^{12}$, —O—$R^{12}$, —S—$R^{12}$, —S(O)—$R^{12}$, —$SO_2$—$R^{12}$, —$SO_2$—$OR^{12}$, —$SO_2$—$NR^{11}R^{12}$, —CO—$OR^{12}$, —CO—$NR^{11}R^{12}$, —O—$SO_2$—$R^{12}$, —N($R^{11}$)—$SO_2$—$R^{12}$, —$NR^{11}R^{12}$, —NH—P(O)($R^{11}$)($OR^{12}$) or —NH—P(O)($OR^{11}$)($OR^{12}$), $R^5$ represents nitro, cyano, fluorine, chlorine or bromine, or represents straight-chain or branched halogenoalkyl having 1 to 3 carbon atoms and 1 to 7 identical or different halogen atoms, and X represents oxygen or sulphur, where $R^8$ and $R^9$ independently of one another each represent hydrogen;

$R^8$ and $R^9$ furthermore represent straight-chain or branched alkyl or alkoxy having in each case 1 to 8 carbon atoms which are in each case optionally monosubstituted, possible substituents in each case being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 4 carbon atoms in the individual alkyl moieties, or heterocyclyl, the heterocyclyl radical being a five- or six-membered, optionally benzo-fused, saturated or aromatic heterocycle having 1 to 3 identical or different heteroatoms—in particular nitrogen, oxygen and/or sulphur;

$R^8$ and $R^9$ furthermore represent in each case straight-chain or branched halogenoalkyl or halogenoalkoxy having in each case 1 to 4 carbon atoms and 1 to 9 identical or different halogen atoms—in particular fluorine, chlorine and/or bromine, $R^8$ and $R^9$ furthermore represent alkenyl or alkinyl having in each case 2 to 6 carbon atoms, which are in each case optionally substituted once to three times by identical or different halogens—in particular fluorine, chlorine and/or bromine;

$R^8$ and $R^9$ furthermore represent cycloalkyl having 3, 5 or 6 carbon atoms which is optionally substituted once to three times by identical or different substituents comprising halogen—in particular fluorine, chlorine and/or bromine—and/or straight-chain or branched alkyl having 1 to 3 carbon atoms;

$R^8$ and $R^9$ furthermore represent phenylalkyl or phenyl having optionally 1 to 3 carbon atoms in the straight-chain or branched alkyl moiety, which are in each case optionally substituted in the phenyl moiety once to three times by identical or different substituents, or represent a saturated or aromatic, five- or six-membered heterocyclyl radical having 1 to 3 identical or different heteroatoms—in particular nitrogen, oxygen and/or sulphur—which is optionally substituted once to three times by identical or different substituents and/or is benzo-fused, possible substituents of phenyl and/or heterocyclyl in each case being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxycarbonyl or alkoximinoalkyl having in each case 1 to 3 carbon atoms in the individual alkyl moieties, and phenyl which is optionally substituted once to three times by identical or different substituents comprising fluorine, chlorine, bromine and/or straight-chain or branched alkyl or alkoxy having in each case 1 to 3 carbon atoms and/or straight-chain or branched halogenoalkyl or halogenoalkoxy having in each case 1 to 3 carbon atoms and 1 to 7 identical or different halogen atoms;

$R^8$ and $R^9$ furthermore represent, together with the nitrogen atom to which they are attached, a saturated or aromatic, five- or six-membered heterocyclyl radical having 1 to 3 identical or different heteroatoms—in particular nitrogen, oxygen and/or sulphur—which is optionally substituted once or twice by identical or different substituents and/or is benzo-fused, possible substituents of heterocyclyl being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxycarbonyl or alkoximinoalkyl having in each case 1 to 3 carbon atoms in the individual alkyl moieties, and phenyl which is optionally substituted once to three times by identical or different substituents comprising fluorine, chlorine, bromine and/or straight-chain or branched alkyl or alkoxy having in each case 1 to 3 carbon atoms and/or straight-chain or branched halogenoalkyl or halogenoalkoxy having in each case 1 to 3 carbon atoms and 1 to 7 identical or different halogen atoms;

$R^{10}$ represents straight-chain or branched alkyl having 1 to 8 carbon atoms which is optionally monosubstituted, possible substituents being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 4 carbon atoms in the individual alkyl moieties, or heterocyclyl, the heterocyclyl radical being a five- or six-membered, optionally benzo-fused, saturated or aromatic heterocycle having 1 to 3 identical or different heteroatoms—in particular nitrogen, oxygen and/or sulphur;

$R^{10}$ furthermore represents straight-chain or branched halogenoalkyl having 1 to 4 carbon atoms and 1 to 9 identical or different halogen atoms—in particular fluorine, chlorine and/or bromine, $R^{10}$ furthermore represents alkenyl or alkinyl having in each case 2 to 6 carbon atoms, which are in each case optionally substituted once to three times by identical or different halogens—in particular fluorine, chlorine and/or bromine;

$R^{10}$ furthermore represents cycloalkyl having 3, 5 or 6 carbon atoms which is optionally substituted once to three times by identical or different substituents comprising halogen—in particular fluorine, chlorine and/or bromine—and/or straight-chain or branched alkyl having 1 to 3 carbon atoms;

$R^{10}$ furthermore represents phenyl alkyl or phenyl having optionally 1 to 3 carbon atoms in the straight-chain or branched alkyl moiety, which are in each case optionally substituted in the phenyl moiety once to three times by identical or different substituents, or represents a saturated or aromatic, five- or six-membered heterocyclyl radical having 1 to 3 identical or different heteroatoms—in particular nitrogen, oxygen and/or sulphur—which is optionally substituted once to three times by identical or different substituents and/or is benzo-fused, possible substituents of phenyl and/or heterocyclyl in each case being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxycarbonyl or alkoximinoalkyl having in each case 1 to 3 carbon atoms in the individual alkyl moieties, and phenyl which is optionally substituted once to three times by identical or different substituents comprising fluorine, chlorine, bromine and/or straight-chain or branched alkyl or alkoxy having in each case 1 to 3 carbon atoms and/or straight-chain or branched halogenoalkyl or halogenoalkoxy having in each case 1 to 3 carbon atoms and 1 to 7 identical or different halogen atoms;

$R^{11}$ represents hydrogen;

$R^{11}$ represents straight-chain or branched alkyl having 1 to 8 carbon atoms which is optionally monosubstituted, possible substituents being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 4 carbon atoms in the individual alkyl moieties, or heterocyclyl, the heterocyclyl radical being a five- or six-membered, optionally benzo-fused, saturated or aromatic heterocycle having 1 to 3 identical or different heteroatoms—in particular nitrogen, oxygen and/or sulphur;

$R^{11}$ furthermore represents straight-chain or branched halogenoalkyl having 1 to 4 carbon atoms and 1 to 9 identical or different halogen atoms—in particular fluorine, chlorine and/or bromine, $R^{11}$ furthermore represents alkenyl or alkinyl having in each case 2 to 6 carbon atoms, which are in each case optionally substituted once to three times by identical or different halogens—in particular fluorine, chlorine and/or bromine;

$R^{11}$ furthermore represents cycloalkyl having 3, 5 or 6 carbon atoms which is optionally substituted once to three times by identical or different substituents comprising halogen—in particular fluorine, chlorine and/or bromine—and/or straight-chain or branched alkyl having 1 to 3 carbon atoms;

$R^{11}$ furthermore represents phenylalkyl or phenyl having optionally 1 to 3 carbon atoms in the straight-chain or branched alkyl moiety, which are in each case optionally substituted in the phenyl moiety once to three times by identical or different substituents, possible substituents of phenyl in each case being:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxycarbonyl or alkoximinoalkyl having in each case 1 to 3 carbon atoms in the individual alkyl moieties, and phenyl which is optionally substituted once to three times by identical or different substituents comprising fluorine, chlorine, bromine and/or straight-chain or branched alkyl or alkoxy having in each case 1 to 3 carbon atoms and/or straight-chain or branched halogenoalkyl or halogenoalkoxy having in each case 1 to 3 carbon atoms and 1 to 7 identical or different halogen atoms;

$R^{12}$ represents hydrogen;

$R^{12}$ represents straight-chain or branched alkyl having 1 to 8 carbon atoms which is optionally monosubstituted, possible substituents being:

cyano, carboxyl, carbamoyl, in each case straight-chain or branched alkoxy, alkoxy-alkoxy, alkylthio, alkylsulphinyl, alkylsulphonyl, alkoxycarbonyl, N-alkylaminocarbonyl, N,N-dialkylaminocarbonyl or alkylsulphonylaminocarbonyl having in each case 1 to 4 carbon atoms in the individual alkyl moieties, or heterocyclyl, the heterocyclyl radical being a five- or six-membered, optionally benzo-fused, saturated or aromatic heterocycle having 1 to 3 identical or different heteroatoms—in particular nitrogen, oxygen and/or sulphur;

$R^{12}$ furthermore represents straight-chain or branched halogenoalkyl having 1 to 4 carbon atoms and 1 to 9 identical or different halogen atoms—in particular fluorine, chlorine and/or bromine, $R^{12}$ furthermore represents alkenyl or alkinyl having in each case 2 to 6 carbon atoms, which are in each case optionally substituted once to three times by identical or different halogens—in particular fluorine, chlorine and/or bromine;

$R^{12}$ furthermore represents cycloalkyl having 3, 5 or 6 carbon atoms which is optionally substituted once to three times by identical or different substituents comprising halogen—in particular fluorine, chlorine and/or bromine—and/or straight-chain or branched alkyl having 1 to 3 carbon atoms;

$R^{12}$ furthermore represents phenylalkyl or phenyl having optionally 1 to 3 carbon atoms in the straight-chain or branched alkyl moiety, which are in each case optionally substituted in the phenyl moiety once to three times by identical or different substituents, or represents a saturated or aromatic, five- or six-membered heterocyclyl radical having 1 to 3 identical or different heteroatoms—in particular nitrogen, oxygen and/or sulphur—which is optionally substituted once to three times by identical or different substituents and/or is benzo-fused, possible substituents of phenyl and/or heterocyclyl being in each case:

fluorine, chlorine, bromine, cyano, nitro, amino, N-acetylamino, in each case straight-chain or branched alkyl, alkoxy, alkylthio, alkylsulphinyl or alkylsulphonyl having in each case 1 to 3 carbon atoms, in each case straight-chain or branched halogenoalkyl, halogenoalkoxy, halogenoalkylthio, halogenoalkylsulphinyl or halogenoalkylsulphonyl having in each case 1 to 3 carbon atoms and 1 to 7 identical or different halogen atoms, in each case straight-chain or branched alkoxycarbonyl or alkoximinoalkyl having in each case 1 to 3 carbon atoms in the individual alkyl moieties, and phenyl which is optionally substituted once to three times by identical or different substituents comprising fluorine, chlorine, bromine and/or straight-chain or branched alkyl or alkoxy having in each case 1 to 3 carbon atoms and/or straight-chain or branched halogenoalkyl or halogenoalkoxy having in each case 1 to 3 carbon atoms and 1 to 7 identical or different halogen atoms;

Individually, apart from the compounds listed in the Preparation Examples, it is possible to mention the following substituted triazolinones of the general formula (I):

TABLE 1

[Structure: A pyrazole/triazole ring system with substituents R¹ on a CH connected to N=N, R² on N, X double-bonded to C, and attached to a phenyl ring bearing R³ (ortho), R⁴ (meta), R⁵ (para), R⁶ (meta'), R⁷ (ortho')]

| $R^1$ | $R^2$ | $R^3$ | $R^4$ | $R^5$ | $R^6$ | $R^7$ | X |
|---|---|---|---|---|---|---|---|
| $NH_2$ | $CH_3$ | H | $-O-C_2H_5$ | CN | H | Cl | O |
| $NH_2$ | $CH_3$ | H | $-S-CH_3$ | CN | H | Cl | O |
| $NH_2$ | $CH_3$ | H | $-S-C_2H_5$ | CN | H | F | O |
| $NH_2$ | $CH_3$ | H | $-NH-SO_2-CH_3$ | CN | H | F | O |
| $NH_2$ | $CH_3$ | H | $-O-CH_2-C\equiv CH$ | CN | H | F | O |
| $NH_2$ | $CH_3$ | Cl | H | $CF_3$ | H | Cl | O |
| $NH_2$ | $CH_3$ | H | $-O-CH_2-CF_3$ | CN | H | F | O |
| $NH_2$ | $CH_3$ | H | $-O-CH_2-CH(CH_2F)_2$ | CN | H | F | O |
| $NH_2$ | $CH_3$ | H | $-O-CH_2-CH_2-O-C_2H_5$ | CN | H | F | O |
| $NH_2$ | $CH_3$ | H | $-S-CH_2-COOCH_3$ | CN | H | F | O |
| $NH_2$ | $CH_3$ | H | $-N(CH_3)_2$ | CN | H | F | O |
| $NO_2$ | $CH_3$ | H | F | CN | H | F | O |
| $NO_2$ | $CH_3$ | H | F | CN | H | Cl | O |
| $NO_2$ | $CH_3$ | H | $-O-CH(CH_3)-C\equiv CH$ | CN | H | F | O |
| $NO_2$ | $CH_3$ | H | $-S-CH_3$ | CN | H | F | O |
| $NO_2$ | $CH_3$ | H | $-NH-SO_2-C_2H_5$ | CN | H | F | O |
| $NO_2$ | $CH_3$ | H | $-O-SO_2-CH_3$ | CN | H | F | O |
| $NO_2$ | $CH_3$ | H | $-O-CH_2-C_6H_5$ | CN | H | F | O |
| $CH_3-NH-$ | H | H | F | $NO_2$ | H | F | O |
| $CH_3-NH-$ | H | H | F | $NO_2$ | H | F | S |
| $CH_3-NH-$ | H | H | F | $NO_2$ | H | Cl | O |
| $CH_3-NH-$ | H | Cl | H | $CF_3$ | H | Cl | O |
| $CH_3-NH-$ | H | H | F | CN | H | F | O |
| $CH_3-NH-$ | H | H | F | CN | H | Cl | O |
| $CH_3-NH-$ | H | H | F | CN | H | Cl | S |
| $CH_3-NH-$ | H | H | F | CN | H | F | S |
| $CH_3-NH-$ | H | Cl | H | $CF_3$ | H | Cl | S |
| $CH_3-NH-$ | H | H | CN | CN | H | H | O |
| $CH_3-NH-$ | H | H | $-O-C_2H_5$ | CN | H | F | O |
| $CH_3-NH-$ | H | H | $-S-CH_3$ | CN | H | F | O |
| $CH_3-NH-$ | H | H | $-O-CH_3$ | CN | H | F | O |
| $CH_3-NH-$ | H | H | $-O-CH_2-C\equiv CH$ | CN | H | F | O |
| $CH_3-NH-$ | H | H | $-S-CH_2-C\equiv CH$ | CN | H | F | O |
| $CH_3-NH-$ | H | H | $-NH-SO_2-CH_3$ | Cl | H | Cl | O |
| $CH_3-NH-$ | H | H | $-NH_2$ | Cl | H | Cl | O |
| $CH_3-NH-$ | H | H | $-O-SO_2-CH_3$ | Cl | H | Cl | O |
| $CH_3-NH-$ | H | H | $-S-C(cyclopropyl)(COOCH_3)$ | Cl | H | Cl | O |
| $CH_3-NH-$ | H | H | $-O-C_6H_4-OCH_3$ (para) | Cl | H | Cl | O |
| $CH_3-NH-$ | H | H | $-NH-CH_3$ | Cl | H | Cl | O |
| $CH_3-NH-$ | $NH_2$ | H | CN | CN | H | H | O |
| $CH_3-NH-$ | $NH_2$ | H | $-O-C_2H_5$ | CN | H | F | O |
| $CH_3-NH-$ | $NH_2$ | H | $-S-CH_3$ | CN | H | F | O |
| $CH_3-NH-$ | $NH_2$ | H | $-NH-CH_3$ | CN | H | F | O |
| $CH_3-NH-$ | $NH_2$ | H | $-O-SO_2-CH_3$ | CN | H | F | O |
| $CH_3-NH-$ | $NH_2$ | H | $-NH-SO_2-CH_3$ | CN | H | F | O |
| $(CH_3)_2N-$ | $CH_3$ | H | F | $NO_2$ | H | F | O |
| $(CH_3)_2N-$ | $CH_3$ | H | F | $NO_2$ | H | Cl | O |
| $(CH_3)_2N-$ | $CH_3$ | H | F | CN | H | H | O |
| $(CH_3)_2N-$ | $CH_3$ | F | H | CN | H | H | O |
| $(CH_3)_2N-$ | $CH_3$ | Cl | H | $CF_3$ | H | Cl | O |
| $(CH_3)_2N-$ | $CH_3$ | Cl | H | Cl | H | H | O |

TABLE 1-continued

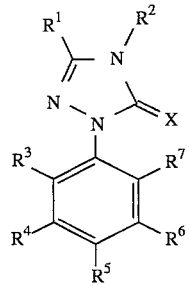

| R¹ | R² | R³ | R⁴ | R⁵ | R⁶ | R⁷ | X |
|---|---|---|---|---|---|---|---|
| (CH₃)₂N— | CH₃ | NO₂ | H | CF₃ | H | NO₂ | O |
| (CH₃)₂N— | CH₃ | Cl | F | CF₃ | H | Cl | O |
| (CH₃)₂N— | CH₃ | H | Cl | CN | Cl | H | O |
| (CH₃)₂N— | CH₃ | H | CN | CN | H | H | O |
| (CH₃)₂N— | CH₃ | Cl | F | NO₂ | H | H | O |
| (CH₃)₂N— | CH₃ | Cl | H | NO₂ | H | Cl | O |
| (CH₃)₂N— | CH₃ | Cl | H | NO₂ | H | F | O |
| (CH₃)₂N— | CH₃ | H | F | CN | H | F | O |
| (CH₃)₂N— | CH₃ | H | F | CN | H | F | O |
| (CH₃)₂N— | CH₃ | H | F | CN | H | Cl | S |
| (CH₃)₂N— | CH₃ | H | F | CN | H | Cl | S |
| (CH₃)₂N— | CH₃ | H | —NH₂ | CN | H | Cl | O |
| (CH₃)₂N— | CH₃ | H | —NH₂ | CN | H | F | O |
| (CH₃)₂N— | CH₃ | H | —NH₂ | CN | H | F | S |
| (CH₃)₂N— | CH₃ | H | —NH—CH₃ | CN | H | F | O |
| (CH₃)₂N— | CH₃ | H | —NH—CH₂—CH=CH₂ | CN | H | F | O |
| (CH₃)₂N— | CH₃ | H | —NH-s-C₄H₉ | CN | H | F | O |
| (CH₃)₂N— | CH₃ | H | —N(CH₃)₂ | CN | H | F | O |
| (CH₃)₂N— | CH₃ | H | —N(CH₂CN)₂ | CN | H | F | O |
| (CH₃)₂N— | CH₃ | H | —NH—SO₂—CH₃ | CN | H | F | O |
| (CH₃)₂N— | CH₃ | H | —NH—SO₂—CH₃ | CN | H | Cl | O |
| (CH₃)₂N— | CH₃ | H | —N(CH₃)—SO₂—CH₃ | CN | H | F | O |
| (CH₃)₂N— | CH₃ | H | —NH—SO₂-n-C₄H₉ | CN | H | F | O |
| (CH₃)₂N— | CH₃ | H | —O—SO₂—CH₃ | CN | H | F | O |
| (CH₃)₂N— | CH₃ | H | —NH—P(O)(CH₃)(OCH₃) | CN | H | F | O |
| (CH₃)₂N— | CH₃ | H | —NH—P(O)(OC₂H₅)₂ | CN | H | F | O |
| (CH₃)₂N— | CH₃ | H | —OH | CN | H | F | O |
| (CH₃)₂N— | CH₃ | H | —O—CH₃ | CN | H | F | O |
| (CH₃)₂N— | CH₃ | H | —O—C₂H₅ | CN | H | F | O |
| (CH₃)₂N— | CH₃ | H | —O—CH₂—C≡CH | CN | H | F | O |
| (CH₃)₂N— | CH₃ | H | —S—C₂H₅ | CN | H | F | O |
| (CH₃)₂N— | CH₃ | H | —O—CH(CH₂F)₂ | CN | H | F | O |
| (CH₃)₂N— | CH₃ | H | —(O—CH₂—CH₂)₂—OCH₃ | CN | H | F | O |
| (CH₃)₂N— | CH₃ | H | —O—CH(CH₃)—COOCH₃ | CN | H | F | O |
| (CH₃)₂N— | CH₃ | H | —O—CH(CH₃)—C≡CH | CN | H | F | O |
| (CH₃)₂N— | CH₃ | H | —S—CH₂—COOCH₃ | CN | H | F | O |
| (CH₃)₂N— | CH₃ | H | —CH₂—CN | CN | H | F | O |
| (CH₃)₂N— | CH₃ | H | 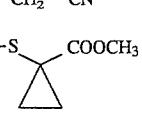 | CN | H | F | O |
| (CH₃)₂N— | CH₃ | H | —O—C₆H₄—OCH(CH₃)—COOC₂H₅ | CN | H | F | O |
| (CH₃)₂N— | CH₃ | H | —O—CH₂—Si(CH₃)₃ | CN | H | F | O |
| (CH₃)₂N— | CH₃ | H | 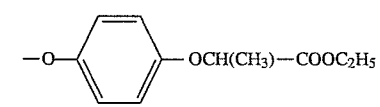 | CN | H | F | O |
| (CH₃)₂N— | CH₃ | H | 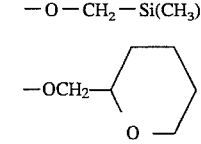 | CN | H | F | O |
| (CH₃)₂N— | CH₃ | H | —O—CHF₂ | CN | H | F | O |
| (CH₃)₂N— | CH₃ | H | —COOCH₃ | CN | H | Cl | O |

TABLE 1-continued

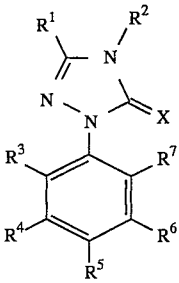

| R¹ | R² | R³ | R⁴ | R⁵ | R⁶ | R⁷ | X |
|---|---|---|---|---|---|---|---|
| $(CH_3)_2N-$ | $CH_3$ | H | $-CO-NH-CH_3$ | CN | H | Cl | O |
| $(CH_3)_2N-$ | $CH_3$ | H | $-CO-N(CH_3)_2$ | CN | H | F | O |
| $(CH_3)_2N-$ | $CH_3$ | H | $-CH_3$ | CN | H | F | O |
| $(CH_3)_2N-$ | $CH_3$ | H | Cl | Cl | H | Cl | O |
| $(CH_3)_2N-$ | $C_2H_5$ | H | F | $NO_2$ | H | F | O |
| $(CH_3)_2N-$ | $C_2H_5$ | H | F | $NO_2$ | H | Cl | O |
| $(CH_3)_2N-$ | $C_2H_5$ | H | F | CN | H | H | O |
| $(CH_3)_2N-$ | $C_2H_5$ | F | H | CN | H | H | O |
| $(CH_3)_2N-$ | $C_2H_5$ | Cl | H | $CF_3$ | H | Cl | O |
| $(CH_3)_2N-$ | $C_2H_5$ | Cl | H | Cl | H | H | O |
| $(CH_3)_2N-$ | $C_2H_5$ | $NO_2$ | H | $CF_3$ | H | $NO_2$ | O |
| $(CH_3)_2N-$ | $C_2H_5$ | Cl | F | $CF_3$ | H | Cl | O |
| $(CH_3)_2N-$ | $C_2H_5$ | H | Cl | CN | Cl | H | O |
| $(CH_3)_2N-$ | $C_2H_5$ | H | CN | CN | H | H | O |
| $(CH_3)_2N-$ | $C_2H_5$ | Cl | F | $NO_2$ | H | H | O |
| $(CH_3)_2N-$ | $C_2H_5$ | Cl | H | $NO_2$ | H | Cl | O |
| $(CH_3)_2N-$ | $C_2H_5$ | Cl | H | $NO_2$ | H | F | O |
| $(CH_3)_2N-$ | $C_2H_5$ | H | F | CN | H | F | O |
| $(CH_3)_2N-$ | $C_2H_5$ | H | F | CN | H | F | S |
| $(CH_3)_2N-$ | $C_2H_5$ | H | F | CN | H | F | S |
| $(CH_3)_2N-$ | $C_2H_5$ | H | F | CN | H | Cl | O |
| $(CH_3)_2N-$ | $C_2H_5$ | H | $-NH_2$ | CN | H | Cl | O |
| $(CH_3)_2N-$ | $C_2H_5$ | H | $-NH_2$ | CN | H | F | O |
| $(CH_3)_2N-$ | $C_2H_5$ | H | $-NH_2$ | CN | H | F | S |
| $(CH_3)_2N-$ | $C_2H_5$ | H | $-NH-CH_3$ | CN | H | F | O |
| $(CH_3)_2N-$ | $C_2H_5$ | H | $-NH-CH_2-CH=CH_2$ | CN | H | F | O |
| $(CH_3)_2N-$ | $C_2H_5$ | H | $-NH\text{-s-}C_4H_9$ | CN | H | F | O |
| $(CH_3)_2N-$ | $C_2H_5$ | H | $-N(CH_3)_2$ | CN | H | F | O |
| $(CH_3)_2N-$ | $C_2H_5$ | H | $-N(CH_2CN)_2$ | CN | H | F | O |
| $(CH_3)_2N-$ | $C_2H_5$ | H | $-NH-SO_2-CH_3$ | CN | H | F | O |
| $(CH_3)_2N-$ | $C_2H_5$ | H | $-NH-SO_2-CH_3$ | CN | H | Cl | O |
| $(CH_3)_2N-$ | $C_2H_5$ | H | $-N(CH_3)-SO_2-CH_3$ | CN | H | F | O |
| $(CH_3)_2N-$ | $C_2H_5$ | H | $-NH-SO_2\text{-n-}C_4H_9$ | CN | H | F | O |
| $(CH_3)_2N-$ | $C_2H_5$ | H | $-O-SO_2-CH_3$ | CN | H | F | O |
| $(CH_3)_2N-$ | $C_2H_5$ | H | $-NH-P(O)(CH_3)(OCH_3)$ | CN | H | F | O |
| $(CH_3)_2N-$ | $C_2H_5$ | H | $-NH-P(O)(OC_2H_5)_2$ | CN | H | F | O |
| $(CH_3)_2N-$ | $C_2H_5$ | H | $-OH$ | CN | H | F | O |
| $(CH_3)_2N-$ | $C_2H_5$ | H | $-O-CH_3$ | CN | H | F | O |
| $(CH_3)_2N-$ | $C_2H_5$ | H | $-O-C_2H_5$ | CN | H | F | O |
| $(CH_3)_2N-$ | $C_2H_5$ | H | $-O-CH_2-C\equiv CH$ | CN | H | F | O |
| $(CH_3)_2N-$ | $C_2H_5$ | H | $-S-C_2H_5$ | CN | H | F | O |
| $(CH_3)_2N-$ | $C_2H_5$ | H | $-O-CH(CH_2F)_2$ | CN | H | F | O |
| $(CH_3)_2N-$ | $C_2H_5$ | H | $-(O-CH_2-CH_2)_2-OCH_3$ | CN | H | F | O |
| $(CH_3)_2N-$ | $C_2H_5$ | H | $-O-CH(CH_3)-COOCH_3$ | CN | H | F | O |
| $(CH_3)_2N-$ | $C_2H_5$ | H | $-O-CH(CH_3)-C\equiv CH$ | CN | H | F | O |
| $(CH_3)_2N-$ | $C_2H_5$ | H | $-S-CH_2-COOCH_3$ | CN | H | F | O |
| $(CH_3)_2N-$ | $C_2H_5$ | H | $-CH_2-CN$ | CN | H | F | O |
| $(CH_3)_2N-$ | $C_2H_5$ | H |  | CN | H | F | O |
| $(CH_3)_2N-$ | $C_2H_5$ | H | 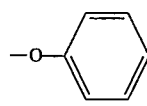 | CN | H | F | O |
| $(CH_3)_2N-$ | $C_2H_5$ | H | $-O-CH_2-Si(CH_3)_3$ | CN | H | F | O |

TABLE 1-continued

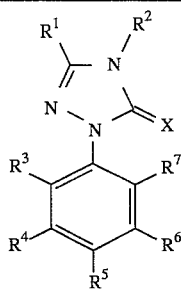

| R¹ | R² | R³ | R⁴ | R⁵ | R⁶ | R⁷ | X |
|---|---|---|---|---|---|---|---|
| (CH₃)₂N— | C₂H₅ | H | -OCH₂-(tetrahydropyran-2-yl) | CN | H | F | O |
| (CH₃)₂N— | C₂H₅ | H | -O-CH₂-(pyridin-2-yl) | CN | H | F | O |
| (CH₃)₂N— | C₂H₅ | H | -O-CHF₂ | CN | H | F | O |
| (CH₃)₂N— | C₂H₅ | H | -COOCH₃ | CN | H | Cl | O |
| (CH₃)₂N— | C₂H₅ | H | -CO-NH-CH₃ | CN | H | Cl | O |
| (CH₃)₂N— | C₂H₅ | H | -CO-N(CH₃)₂ | CN | H | F | O |
| (CH₃)₂N— | C₂H₅ | H | -CH₃ | CN | H | F | O |
| (CH₃)₂N— | C₂H₅ | H | Cl | Cl | H | Cl | O |
| (CH₃)₂N— | i-C₃H₇ | H | F | NO₂ | H | H | O |
| (CH₃)₂N— | i-C₃H₇ | H | F | NO₂ | H | Cl | O |
| (CH₃)₂N— | i-C₃H₇ | H | F | CN | H | H | O |
| (CH₃)₂N— | i-C₃H₇ | F | H | CN | H | H | O |
| (CH₃)₂N— | i-C₃H₇ | Cl | H | CF₃ | H | Cl | O |
| (CH₃)₂N— | i-C₃H₇ | Cl | H | Cl | H | H | O |
| (CH₃)₂N— | i-C₃H₇ | NO₂ | H | CF₃ | H | NO₂ | O |
| (CH₃)₂N— | i-C₃H₇ | Cl | F | CF₃ | H | Cl | O |
| (CH₃)₂N— | i-C₃H₇ | H | Cl | CN | Cl | H | O |
| (CH₃)₂N— | i-C₃H₇ | H | CN | CN | H | H | O |
| (CH₃)₂N— | i-C₃H₇ | Cl | F | NO₂ | H | H | O |
| (CH₃)₂N— | i-C₃H₇ | Cl | H | NO₂ | H | Cl | O |
| (CH₃)₂N— | i-C₃H₇ | Cl | H | NO₂ | H | F | O |
| (CH₃)₂N— | i-C₃H₇ | H | F | CN | H | F | O |
| (CH₃)₂N— | i-C₃H₇ | H | F | CN | H | F | S |
| (CH₃)₂N— | i-C₃H₇ | H | F | CN | H | Cl | S |
| (CH₃)₂N— | i-C₃H₇ | H | F | CN | H | Cl | O |
| (CH₃)₂N— | i-C₃H₇ | H | -NH₂ | CN | H | Cl | O |
| (CH₃)₂N— | i-C₃H₇ | H | -NH₂ | CN | H | F | O |
| (CH₃)₂N— | i-C₃H₇ | H | -NH₂ | CN | H | F | S |
| (CH₃)₂N— | i-C₃H₇ | H | -NH-CH₃ | CN | H | F | O |
| (CH₃)₂N— | i-C₃H₇ | H | -NH-CH₂-CH=CH₂ | CN | H | F | O |
| (CH₃)₂N— | i-C₃H₇ | H | -NH-s-C₄H₉ | CN | H | F | O |
| (CH₃)₂N— | i-C₃H₇ | H | -N(CH₃)₂ | CN | H | F | O |
| (CH₃)₂N— | i-C₃H₇ | H | -N(CH₂CN)₂ | CN | H | F | O |
| (CH₃)₂N— | i-C₃H₇ | H | -NH-SO₂-CH₃ | CN | H | F | O |
| (CH₃)₂N— | i-C₃H₇ | H | -NH-SO₂-CH₃ | CN | H | Cl | O |
| (CH₃)₂N— | i-C₃H₇ | H | -N(CH₃)-SO₂-CH₃ | CN | H | F | O |
| (CH₃)₂N— | i-C₃H₇ | H | -NH-SO₂-n-C₄H₉ | CN | H | F | O |
| (CH₃)₂N— | i-C₃H₇ | H | -O-SO₂-CH₃ | CN | H | F | O |
| (CH₃)₂N— | i-C₃H₇ | H | -NH-P(O)(CH₃)(OCH₃) | CN | H | F | O |
| (CH₃)₂N— | i-C₃H₇ | H | -NH-P(O)(OC₂H₅)₂ | CN | H | F | O |
| (CH₃)₂N— | i-C₃H₇ | H | -OH | CN | H | F | O |
| (CH₃)₂N— | i-C₃H₇ | H | -O-CH₃ | CN | H | F | O |
| (CH₃)₂N— | i-C₃H₇ | H | -O-C₂H₅ | CN | H | F | O |
| (CH₃)₂N— | i-C₃H₇ | H | -O-CH₂-C≡CH | CN | H | F | O |
| (CH₃)₂N— | i-C₃H₇ | H | -S-C₂H₅ | CN | H | F | O |
| (CH₃)₂N— | i-C₃H₇ | H | -O-CH(CH₂F)₂ | CN | H | F | O |
| (CH₃)₂N— | i-C₃H₇ | H | -(O-CH₂-CH₂)₂-OCH₃ | CN | H | F | O |
| (CH₃)₂N— | i-C₃H₇ | H | -O-CH(CH₃)-COOCH₃ | CN | H | F | O |
| (CH₃)₂N— | i-C₃H₇ | H | -O-CH(CH₃)-C≡CH | CN | H | F | O |
| (CH₃)₂N— | i-C₃H₇ | H | -S-CH₂-COOCH₃ | CN | H | F | O |
| (CH₃)₂N— | i-C₃H₇ | H | -CH₂-CN | CN | H | F | O |

TABLE 1-continued

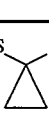

| R¹ | R² | R³ | R⁴ | R⁵ | R⁶ | R⁷ | X |
|---|---|---|---|---|---|---|---|
| (CH₃)₂N— | i-C₃H₇ | H | 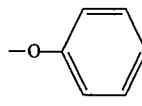 | CN | H | F | O |
| (CH₃)₂N— | i-C₃H₇ | H | 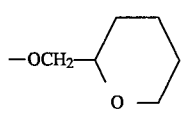 | CN | H | F | O |
| (CH₃)₂N— | i-C₃H₇ | H | —O—CH₂—Si(CH₃)₃ | CN | H | F | O |
| (CH₃)₂N— | i-C₃H₇ | H | 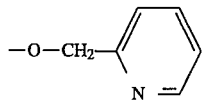 | CN | H | F | O |
| (CH₃)₂N— | i-C₃H₇ | H | 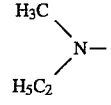 | CN | H | F | O |
| (CH₃)₂N— | i-C₃H₇ | H | —O—CHF₂ | CN | H | F | O |
| (CH₃)₂N— | i-C₃H₇ | H | —COOCH₃ | CN | H | Cl | O |
| (CH₃)₂N— | i-C₃H₇ | H | —CO—NH—CH₃ | CN | H | Cl | O |
| (CH₃)₂N— | i-C₃H₇ | H | —CO—N(CH₃)₂ | CN | H | F | O |
| (CH₃)₂N— | i-C₃H₇ | H | —CH₃ | CN | H | F | O |
| (CH₃)₂N— | i-C₃H₇ | H | Cl | Cl | H | Cl | O |
| 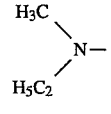 | CH₃ | H | F | NO₂ | H | F | O |
| 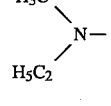 | CH₃ | H | F | NO₂ | H | Cl | O |
| 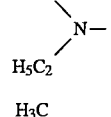 | CH₃ | H | F | CN | H | H | O |
| 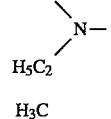 | CH₃ | F | H | CN | H | H | O |
| 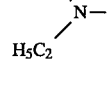 | CH₃ | Cl | H | CF₃ | H | Cl | O |
| 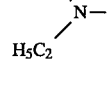 | CH₃ | Cl | H | Cl | H | H | O |

TABLE 1-continued
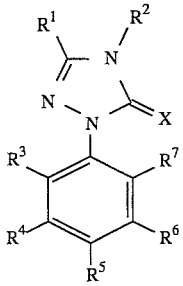
| R¹ | R² | R³ | R⁴ | R⁵ | R⁶ | R⁷ | X |
|---|---|---|---|---|---|---|---|
| H₃C\N—/H₅C₂ | CH₃ | NO₂ | H | CF₃ | H | NO₂ | O |
| H₃C\N—/H₅C₂ | CH₃ | Cl | F | CF₃ | H | Cl | O |
| H₃C\N—/H₅C₂ | CH₃ | H | Cl | CN | Cl | H | O |
| H₃C\N—/H₅C₂ | CH₃ | H | CN | CN | H | H | O |
| H₃C\N—/H₅C₂ | CH₃ | Cl | F | NO₂ | H | H | O |
| H₃C\N—/H₅C₂ | CH₃ | Cl | H | NO₂ | H | Cl | O |
| H₃C\N—/H₅C₂ | CH₃ | Cl | H | NO₂ | H | F | O |
| H₃C\N—/H₅C₂ | CH₃ | H | F | CN | H | F | O |
| H₃C\N—/H₅C₂ | CH₃ | H | F | CN | H | F | S |
| H₃C\N—/H₅C₂ | CH₃ | H | F | CN | H | Cl | S |
| H₃C\N—/H₅C₂ | CH₃ | H | F | CN | H | Cl | O |

TABLE 1-continued

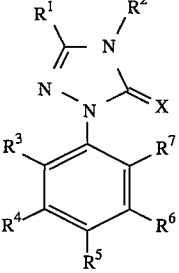

| R¹ | R² | R³ | R⁴ | R⁵ | R⁶ | R⁷ | X |
|---|---|---|---|---|---|---|---|
| H₃C\N—/H₅C₂ | CH₃ | H | —NH₂ | CN | H | Cl | O |
| H₃C\N—/H₅C₂ | CH₃ | H | —NH₂ | CN | H | F | O |
| H₃C\N—/H₅C₂ | CH₃ | H | —NH₂ | CN | H | F | S |
| H₃C\N—/H₅C₂ | CH₃ | H | —NH—CH₃ | CN | H | F | O |
| H₃C\N—/H₅C₂ | CH₃ | H | —NH—CH₂—CH=CH₂ | CN | H | F | O |
| H₃C\N—/H₅C₂ | CH₃ | H | —NH-s-C₄H₉ | CN | H | F | O |
| H₃C\N—/H₅C₂ | CH₃ | H | —N(CH₃)₂ | CN | H | F | O |
| H₃C\N—/H₅C₂ | CH₃ | H | —N(CH₂CN)₂ | CN | H | F | O |
| H₃C\N—/H₅C₂ | CH₃ | H | —NH—SO₂—CH₃ | CN | H | F | O |
| H₃C\N—/H₅C₂ | CH₃ | H | —NH—SO₂—CH₃ | CN | H | Cl | O |
| H₃C\N—/H₅C₂ | CH₃ | H | —N(CH₃)—SO₂CH₃ | CN | H | F | O |

TABLE 1-continued

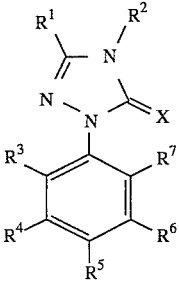

| R¹ | R² | R³ | R⁴ | R⁵ | R⁶ | R⁷ | X |
|---|---|---|---|---|---|---|---|
| H₃C\N—/H₅C₂ | CH₃ | H | —NH—SO₂-n-C₄H₉ | CN | H | F | O |
| H₃C\N—/H₅C₂ | CH₃ | H | —O—SO₂—CH₃ | CN | H | F | O |
| H₃C\N—/H₅C₂ | CH₃ | H | —NH—P(O)(CH₃)(OCH₃) | CN | H | F | O |
| H₃C\N—/H₅C₂ | CH₃ | H | —NH—P(O)(OC₂H₅)₂ | CN | H | F | O |
| H₃C\N—/H₅C₂ | CH₃ | H | —OH | CN | H | F | O |
| H₃C\N—/H₅C₂ | CH₃ | H | —O—CH₃ | CN | H | F | O |
| H₃C\N—/H₅C₂ | CH₃ | H | —O—C₂H₅ | CN | H | F | O |
| H₃C\N—/H₅C₂ | CH₃ | H | —O—CH₂—C≡CH | CN | H | F | O |
| H₃C\N—/H₅C₂ | CH₃ | H | —S—C₂H₅ | CN | H | F | O |
| H₃C\N—/H₅C₂ | CH₃ | H | —O—CH(CH₂F)₂ | CN | H | F | O |
| H₃C\N—/H₅C₂ | CH₃ | H | —(O—CH₂—CH₂)₂—OCH₃ | CN | H | F | O |

TABLE 1-continued

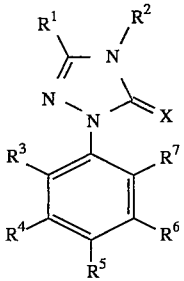

| R¹ | R² | R³ | R⁴ | R⁵ | R⁶ | R⁷ | X |
|---|---|---|---|---|---|---|---|
| H₃C\N(H₅C₂)—N— | CH₃ | H | —O—CH(CH₃)—COOCH₃ | CN | H | F | O |
| H₃C\N(H₅C₂)—N— | CH₃ | H | —O—CH(CH₃)—C≡CH | CN | H | F | O |
| H₃C\N(H₅C₂)—N— | CH₃ | H | —S—CH₂—COOCH₃ | CN | H | F | O |
| H₃C\N(H₅C₂)—N— | CH₃ | H | —CH₂—CN | CN | H | F | O |
| H₃C\N(H₅C₂)—N— | CH₃ | H | —S—(cyclopropyl-COOCH₃) | CN | H | F | O |
| H₃C\N(H₅C₂)—N— | CH₃ | H | —O—C₆H₄—OCH(CH₃)—COOC₂H₅ | CN | H | F | O |
| H₃C\N(H₅C₂)—N— | CH₃ | H | —O—CH₂—Si(CH₃)₃ | CN | H | F | O |
| H₃C\N(H₅C₂)—N— | CH₃ | H | —OCH₂—(tetrahydropyran-2-yl) | CN | H | F | O |
| H₃C\N(H₅C₂)—N— | CH₃ | H | —O—CH₂—(pyridin-2-yl) | CN | H | F | O |
| H₃C\N(H₅C₂)—N— | CH₃ | H | —O—CHF₂ | CN | H | F | O |
| H₃C\N(H₅C₂)—N— | CH₃ | H | —COOCH₃ | CN | H | Cl | O |

TABLE 1-continued
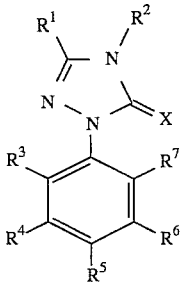
| R¹ | R² | R³ | R⁴ | R⁵ | R⁶ | R⁷ | X |
|---|---|---|---|---|---|---|---|
| 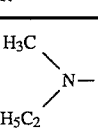 | CH₃ | H | —CO—NH—CH₃ | CN | H | Cl | O |
| 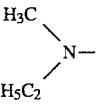 | CH₃ | H | —CO—N(CH₃)₂ | CN | H | F | O |
| 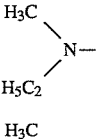 | CH₃ | H | —CH₃ | CN | H | F | O |
| 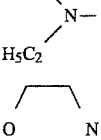 | CH₃ | H | Cl | Cl | H | Cl | O |
| 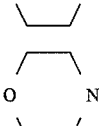 | CH₃ | H | F | NO₂ | H | F | O |
| 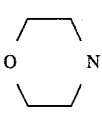 | CH₃ | H | F | NO₂ | H | Cl | O |
| 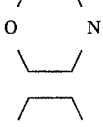 | CH₃ | H | F | CN | H | H | O |
| 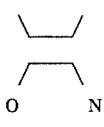 | CH₃ | F | H | CN | H | H | O |
| 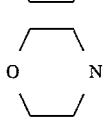 | CH₃ | Cl | H | CF₃ | H | Cl | O |
| 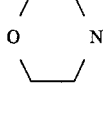 | CH₃ | Cl | H | Cl | H | H | O |
|  | CH₃ | NO₂ | H | CF₃ | H | NO₂ | O |
|  | CH₃ | Cl | F | CF₃ | H | Cl | O |

TABLE 1-continued
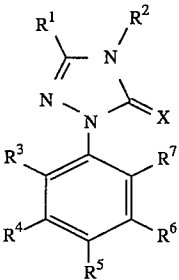
| R¹ | R² | R³ | R⁴ | R⁵ | R⁶ | R⁷ | X |
|---|---|---|---|---|---|---|---|
|  | CH₃ | H | Cl | CN | Cl | H | O |
|  | CH₃ | H | CN | CN | H | H | O |
|  | CH₃ | Cl | F | NO₂ | H | H | O |
|  | CH₃ | Cl | H | NO₂ | H | Cl | O |
|  | CH₃ | Cl | H | NO₂ | H | F | O |
|  | CH₃ | H | F | CN | H | F | O |
|  | CH₃ | H | F | CN | H | F | S |
|  | CH₃ | H | F | CN | H | Cl | S |
|  | CH₃ | H | F | CN | H | Cl | O |
|  | CH₃ | H | —NH₂ | CN | H | Cl | O |
|  | CH₃ | H | —NH₂ | CN | H | F | O |
|  | CH₃ | H | —NH₂ | CN | H | F | S |

TABLE 1-continued

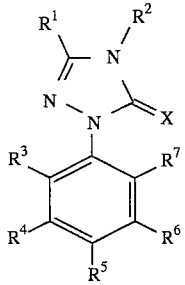

| R¹ | R² | R³ | R⁴ | R⁵ | R⁶ | R⁷ | X |
|---|---|---|---|---|---|---|---|
| O(CH₂CH₂)₂N— | CH₃ | H | —NH—CH₃ | CN | H | F | O |
| O(CH₂CH₂)₂N— | CH₃ | H | —NH—CH₂—CH=CH₂ | CN | H | F | O |
| O(CH₂CH₂)₂N— | CH₃ | H | —NH-s-C₄H₉ | CN | H | F | O |
| O(CH₂CH₂)₂N— | CH₃ | H | —N(CH₃)₂ | CN | H | F | O |
| O(CH₂CH₂)₂N— | CH₃ | H | —N(CH₂CN)₂ | CN | H | F | O |
| O(CH₂CH₂)₂N— | CH₃ | H | —NH—SO₂—CH₃ | CN | H | F | O |
| O(CH₂CH₂)₂N— | CH₃ | H | —NH—SO₂—CH₃ | CN | H | Cl | O |
| O(CH₂CH₂)₂N— | CH₃ | H | —N(CH₃)—SO₂—CH₃ | CN | H | F | O |
| O(CH₂CH₂)₂N— | CH₃ | H | —NH—SO₂-n-C₄H₉ | CN | H | F | O |
| O(CH₂CH₂)₂N— | CH₃ | H | —O—SO₂—CH₃ | CN | H | F | O |
| O(CH₂CH₂)₂N— | CH₃ | H | —NH—P(O)(CH₃)(OCH₃) | CN | H | F | O |
| O(CH₂CH₂)₂N— | CH₃ | H | —NH—P(O)(OC₂H₅)₂ | CN | H | F | O |

TABLE 1-continued

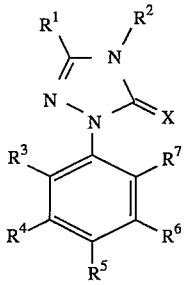

| R¹ | R² | R³ | R⁴ | R⁵ | R⁶ | R⁷ | X |
|---|---|---|---|---|---|---|---|
| morpholino | CH₃ | H | —OH | CN | H | F | O |
| morpholino | CH₃ | H | —O—CH₃ | CN | H | F | O |
| morpholino | CH₃ | H | —O—C₂H₅ | CN | H | F | O |
| morpholino | CH₃ | H | —O—CH₂—C≡CH | CN | H | F | O |
| morpholino | CH₃ | H | —S—C₂H₅ | CN | H | F | O |
| morpholino | CH₃ | H | —O—CH(CH₂F)₂ | CN | H | F | O |
| morpholino | CH₃ | H | —(O—CH₂—CH₂)₂—OCH₃ | CN | H | F | O |
| morpholino | CH₃ | H | —O—CH(CH₃)—COOCH₃ | CN | H | F | O |
| morpholino | CH₃ | H | —O—CH(CH₃)—C≡CH | CN | H | F | O |
| morpholino | CH₃ | H | —S—CH₂—COOCH₃ | CN | H | F | O |
| morpholino | CH₃ | H | —CH₂—CN | CN | H | F | O |
| morpholino | CH₃ | H | —S—C(cyclopropyl)—COOCH₃ | CN | H | F | O |

TABLE 1-continued

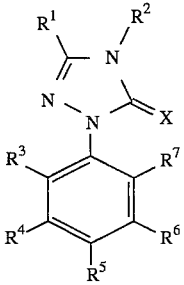

| R¹ | R² | R³ | R⁴ | R⁵ | R⁶ | R⁷ | X |
|---|---|---|---|---|---|---|---|
| morpholino-N— | CH$_3$ | H | —O—C$_6$H$_4$—OCH(CH$_3$)—COOC$_2$H$_5$ | CN | H | F | O |
| morpholino-N— | CH$_3$ | H | —O—CH$_2$—Si(CH$_3$)$_3$ | CN | H | F | O |
| morpholino-N— | CH$_3$ | H | —OCH$_2$-(tetrahydropyran-2-yl) | CN | H | F | O |
| morpholino-N— | CH$_3$ | H | —O—CH$_2$-(pyridin-2-yl) | CN | H | F | O |
| morpholino-N— | CH$_3$ | H | —O—CHF$_2$ | CN | H | F | O |
| morpholino-N— | CH$_3$ | H | —COOCH$_3$ | CN | H | Cl | O |
| morpholino-N— | CH$_3$ | H | —CO—NH—CH$_3$ | CN | H | Cl | O |
| morpholino-N— | CH$_3$ | H | —CO—N(CH$_3$)$_2$ | CN | H | F | O |
| morpholino-N— | CH$_3$ | H | —CH$_3$ | CN | H | F | O |
| morpholino-N— | CH$_3$ | H | Cl | Cl | H | Cl | O |
| (CH$_3$)$_2$N— | NH$_2$ | H | F | NO$_2$ | H | F | O |
| (CH$_3$)$_2$N— | NH$_2$ | H | F | NO$_2$ | H | Cl | O |
| (CH$_3$)$_2$N— | NH$_2$ | H | F | CN | H | H | O |
| (CH$_3$)$_2$N— | NH$_2$ | F | H | CN | H | H | O |
| (CH$_3$)$_2$N— | NH$_2$ | Cl | H | CF$_3$ | H | Cl | O |
| (CH$_3$)$_2$N— | NH$_2$ | Cl | H | Cl | H | H | O |
| (CH$_3$)$_2$N— | NH$_2$ | NO$_2$ | H | CF$_3$ | H | NO$_2$ | O |
| (CH$_3$)$_2$N— | NH$_2$ | Cl | F | CF$_3$ | H | Cl | O |
| (CH$_3$)$_2$N— | NH$_2$ | H | Cl | CN | Cl | H | O |

TABLE 1-continued

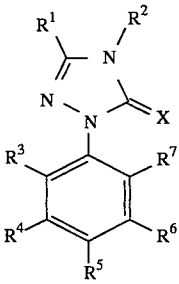

| R¹ | R² | R³ | R⁴ | R⁵ | R⁶ | R⁷ | X |
|---|---|---|---|---|---|---|---|
| $(CH_3)_2N-$ | $NH_2$ | H | CN | CN | H | H | O |
| $(CH_3)_2N-$ | $NH_2$ | Cl | F | $NO_2$ | H | H | O |
| $(CH_3)_2N-$ | $NH_2$ | Cl | H | $NO_2$ | H | Cl | O |
| $(CH_3)_2N-$ | $NH_2$ | Cl | H | $NO_2$ | H | F | O |
| $(CH_3)_2N-$ | $NH_2$ | H | F | CN | H | F | O |
| $(CH_3)_2N-$ | $NH_2$ | H | F | CN | H | F | S |
| $(CH_3)_2N-$ | $NH_2$ | H | F | CN | H | Cl | S |
| $(CH_3)_2N-$ | $NH_2$ | H | F | CN | H | Cl | O |
| $(CH_3)_2N-$ | $NH_2$ | H | $-NH_2$ | CN | H | Cl | O |
| $(CH_3)_2N-$ | $NH_2$ | H | $-NH_2$ | CN | H | F | O |
| $(CH_3)_2N-$ | $NH_2$ | H | $-NH_2$ | CN | H | F | S |
| $(CH_3)_2N-$ | $NH_2$ | H | $-NH-CH_3$ | CN | H | F | O |
| $(CH_3)_2N-$ | $NH_2$ | H | $-NH-CH_2-CH=CH_2$ | CN | H | F | O |
| $(CH_3)_2N-$ | $NH_2$ | H | $-NH-s-C_4H_9$ | CN | H | F | O |
| $(CH_3)_2N-$ | $NH_2$ | H | $-N(CH_3)_2$ | CN | H | F | O |
| $(CH_3)_2N-$ | $NH_2$ | H | $-N(CH_2CN)_2$ | CN | H | F | O |
| $(CH_3)_2N-$ | $NH_2$ | H | $-NH-SO_2-CH_3$ | CN | H | F | O |
| $(CH_3)_2N-$ | $NH_2$ | H | $-NH-SO_2-CH_3$ | CN | H | Cl | O |
| $(CH_3)_2N-$ | $NH_2$ | H | $-N(CH_3)-SO_2-CH_3$ | CN | H | F | O |
| $(CH_3)_2N-$ | $NH_2$ | H | $-NH-SO_2-n-C_4H_9$ | CN | H | F | O |
| $(CH_3)_2N-$ | $NH_2$ | H | $-O-SO_2-CH_3$ | CN | H | F | O |
| $(CH_3)_2N-$ | $NH_2$ | H | $-NH-P(O)(CH_3)(OCH_3)$ | CN | H | F | O |
| $(CH_3)_2N-$ | $NH_2$ | H | $-NH-P(O)(OC_2H_5)_2$ | CN | H | F | O |
| $(CH_3)_2N-$ | $NH_2$ | H | $-OH$ | CN | H | F | O |
| $(CH_3)_2N-$ | $NH_2$ | H | $-O-CH_3$ | CN | H | F | O |
| $(CH_3)_2N-$ | $NH_2$ | H | $-O-C_2H_5$ | CN | H | F | O |
| $(CH_3)_2N-$ | $NH_2$ | H | $-O-CH_2-C\equiv CH$ | CN | H | F | O |
| $(CH_3)_2N-$ | $NH_2$ | H | $-S-C_2H_5$ | CN | H | F | O |
| $(CH_3)_2N-$ | $NH_2$ | H | $-O-CH(CH_2F)_2$ | CN | H | F | O |
| $(CH_3)_2N-$ | $NH_2$ | H | $-(O-CH_2-CH_2)_2-OCH_3$ | CN | H | F | O |
| $(CH_3)_2N-$ | $NH_2$ | H | $-O-CH(CH_3)-COOCH_3$ | CN | H | F | O |
| $(CH_3)_2N-$ | $NH_2$ | H | $-O-CH(CH_3)-C\equiv CH$ | CN | H | F | O |
| $(CH_3)_2N-$ | $NH_2$ | H | $-S-CH_2-COOCH_3$ | CN | H | F | O |
| $(CH_3)_2N-$ | $NH_2$ | H | $-CH_2-CN$ | CN | H | F | O |
| $(CH_3)_2N-$ | $NH_2$ | H |  | CN | H | F | O |
| $(CH_3)_2N-$ | $NH_2$ | H | 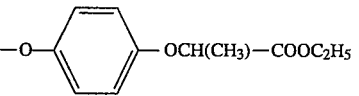 | CN | H | F | O |
| $(CH_3)_2N-$ | $NH_2$ | H | $-O-CH_2-Si(CH_3)_3$ | CN | H | F | O |
| $(CH_3)_2N-$ | $NH_2$ | H | 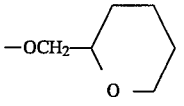 | CN | H | F | O |
| $(CH_3)_2N-$ | $NH_2$ | H | 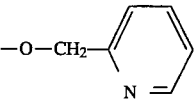 | CN | H | F | O |
| $(CH_3)_2N-$ | $NH_2$ | H | $-O-CHF_2$ | CN | H | F | O |
| $(CH_3)_2N-$ | $NH_2$ | H | $-COOCH_3$ | CN | H | Cl | O |
| $(CH_3)_2N-$ | $NH_2$ | H | $-CO-NH-CH_3$ | CN | H | Cl | O |
| $(CH_3)_2N-$ | $NH_2$ | H | $-CO-N(CH_3)_2$ | CN | H | F | O |

TABLE 1-continued

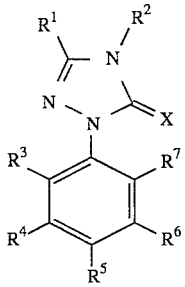

| R¹ | R² | R³ | R⁴ | R⁵ | R⁶ | R⁷ | X |
|---|---|---|---|---|---|---|---|
| (CH₃)₂N— | NH₂ | H | —CH₃ | CN | H | F | O |
| (CH₃)₂N— | NH₂ | H | Cl | Cl | H | Cl | O |
| (CH₃)₂N— | H | H | F | NO₂ | H | F | O |
| (CH₃)₂N— | H | H | F | NO₂ | H | Cl | O |
| (CH₃)₂N— | H | H | F | CN | H | H | O |
| (CH₃)₂N— | H | F | H | CN | H | H | O |
| (CH₃)₂N— | H | Cl | H | CF₃ | H | Cl | O |
| (CH₃)₂N— | H | Cl | H | Cl | H | H | O |
| (CH₃)₂N— | H | NO₂ | H | CF₃ | H | NO₂ | O |
| (CH₃)₂N— | H | Cl | F | CF₃ | H | Cl | O |
| (CH₃)₂N— | H | H | Cl | CN | Cl | H | O |
| (CH₃)₂N— | H | H | CN | CN | H | H | O |
| (CH₃)₂N— | H | Cl | F | NO₂ | H | H | O |
| (CH₃)₂N— | H | Cl | H | NO₂ | H | Cl | O |
| (CH₃)₂N— | H | Cl | H | NO₂ | H | F | O |
| (CH₃)₂N— | H | H | F | CN | H | F | O |
| (CH₃)₂N— | H | H | F | CN | H | F | S |
| (CH₃)₂N— | H | H | F | CN | H | Cl | S |
| (CH₃)₂N— | H | H | F | CN | H | Cl | O |
| (CH₃)₂N— | H | H | —NH₂ | CN | H | Cl | O |
| (CH₃)₂N— | H | H | —NH₂ | CN | H | F | O |
| (CH₃)₂N— | H | H | —NH₂ | CN | H | F | S |
| (CH₃)₂N— | H | H | —NH—CH₃ | CN | H | F | O |
| (CH₃)₂N— | H | H | —NH—CH₂—CH=CH₂ | CN | H | F | O |
| (CH₃)₂N— | H | H | —NH-s-C₄H₉ | CN | H | F | O |
| (CH₃)₂N— | H | H | —N(CH₃)₂ | CN | H | F | O |
| (CH₃)₂N— | H | H | —N(CH₂CN)₂ | CN | H | F | O |
| (CH₃)₂N— | H | H | —NH—SO₂—CH₃ | CN | H | F | O |
| (CH₃)₂N— | H | H | —NH—SO₂—CH₃ | CN | H | Cl | O |
| (CH₃)₂N— | H | H | —N(CH₃)—SO₂—CH₃ | CN | H | F | O |
| (CH₃)₂N— | H | H | —NH—SO₂-n-C₄H₉ | CN | H | F | O |
| (CH₃)₂N— | H | H | —O—SO₂—CH₃ | CN | H | F | O |
| (CH₃)₂N— | H | H | —NH—P(O)(CH₃)(OCH₃) | CN | H | F | O |
| (CH₃)₂N— | H | H | —NH—P(O)(OC₂H₅)₂ | CN | H | F | O |
| (CH₃)₂N— | H | H | —OH | CN | H | F | O |
| (CH₃)₂N— | H | H | —O—CH₃ | CN | H | F | O |
| (CH₃)₂N— | H | H | —O—C₂H₅ | CN | H | F | O |
| (CH₃)₂N— | H | H | —O—CH₂—C≡CH | CN | H | F | O |
| (CH₃)₂N— | H | H | —S—C₂H₅ | CN | H | F | O |
| (CH₃)₂N— | H | H | —O—CH(CH₂F)₂ | CN | H | F | O |
| (CH₃)₂N— | H | H | —(O—CH₂—CH₂)₂—OCH₃ | CN | H | F | O |
| (CH₃)₂N— | H | H | —O—CH(CH₃)—COOCH₃ | CN | H | F | O |
| (CH₃)₂N— | H | H | —O—CH(CH₃)—C≡CH | CN | H | F | O |
| (CH₃)₂N— | H | H | —S—CH₂—COOCH₃ | CN | H | F | O |
| (CH₃)₂N— | H | H | —CH₂—CN | CN | H | F | O |
| (CH₃)₂N— | H | H | 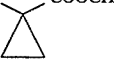 | CN | H | F | O |
| (CH₃)₂N— | H | H | 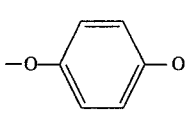 | CN | H | F | O |
| (CH₃)₂N— | H | H | —O—CH₂—Si(CH₃)₃ | CN | H | F | O |

TABLE 1-continued

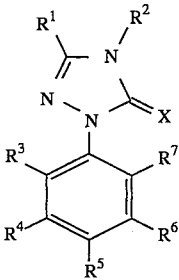

| R¹ | R² | R³ | R⁴ | R⁵ | R⁶ | R⁷ | X |
|---|---|---|---|---|---|---|---|
| (CH₃)₂N— | H | H | —OCH₂-(tetrahydropyran) | CN | H | F | O |
| (CH₃)₂N— | H | H | —O—CH₂-(2-pyridyl) | CN | H | F | O |
| (CH₃)₂N— | H | H | —O—CHF₂ | CN | H | F | O |
| (CH₃)₂N— | H | H | —COOCH₃ | CN | H | Cl | O |
| (CH₃)₂N— | H | H | —CO—NH—CH₃ | CN | H | Cl | O |
| (CH₃)₂N— | H | H | —CO—N(CH₃)₂ | CN | H | F | O |
| (CH₃)₂N— | H | H | —CH₃ | CN | H | F | O |
| (CH₃)₂N— | H | H | Cl | Cl | H | Cl | O |
| (CH₃)₂N— | (CH₃)₂N— | H | F | NO₂ | H | F | O |
| (CH₃)₂N— | (CH₃)₂N— | H | F | NO₂ | H | Cl | O |
| (CH₃)₂N— | (CH₃)₂N— | H | F | CN | H | H | O |
| (CH₃)₂N— | (CH₃)₂N— | F | H | CN | H | H | O |
| (CH₃)₂N— | (CH₃)₂N— | Cl | H | CF₃ | H | Cl | O |
| (CH₃)₂N— | (CH₃)₂N— | Cl | H | Cl | H | H | O |
| (CH₃)₂N— | (CH₃)₂N— | NO₂ | H | CF₃ | H | NO₂ | O |
| (CH₃)₂N— | (CH₃)₂N— | Cl | F | CF₃ | H | Cl | O |
| (CH₃)₂N— | (CH₃)₂N— | H | Cl | CN | Cl | H | O |
| (CH₃)₂N— | (CH₃)₂N— | H | CN | CN | H | H | O |
| (CH₃)₂N— | (CH₃)₂N— | Cl | F | NO₂ | H | H | O |
| (CH₃)₂N— | (CH₃)₂N— | Cl | H | NO₂ | H | Cl | O |
| (CH₃)₂N— | (CH₃)₂N— | Cl | H | NO₂ | H | F | O |
| (CH₃)₂N— | (CH₃)₂N— | H | F | CN | H | F | O |
| (CH₃)₂N— | (CH₃)₂N— | H | F | CN | H | F | S |
| (CH₃)₂N— | (CH₃)₂N— | H | F | CN | H | Cl | S |
| (CH₃)₂N— | (CH₃)₂N— | H | F | CN | H | Cl | O |
| (CH₃)₂N— | (CH₃)₂N— | H | —NH₂ | CN | H | Cl | O |
| (CH₃)₂N— | (CH₃)₂N— | H | —NH₂ | CN | H | F | O |
| (CH₃)₂N— | (CH₃)₂N— | H | —NH₂ | CN | H | F | S |
| (CH₃)₂N— | (CH₃)₂N— | H | —NH—CH₃ | CN | H | F | O |
| (CH₃)₂N— | (CH₃)₂N— | H | —NH—CH₂—CH=CH₂ | CN | H | F | O |
| (CH₃)₂N— | (CH₃)₂N— | H | —NH-s-C₄H₉ | CN | H | F | O |
| (CH₃)₂N— | (CH₃)₂N— | H | —N(CH₃)₂ | CN | H | F | O |
| (CH₃)₂N— | (CH₃)₂N— | H | —N(CH₂CN)₂ | CN | H | F | O |
| (CH₃)₂N— | (CH₃)₂N— | H | —NH—SO₂—CH₃ | CN | H | F | O |
| (CH₃)₂N— | (CH₃)₂N— | H | —NH—SO₂—CH₃ | CN | H | Cl | O |
| (CH₃)₂N— | (CH₃)₂N— | H | —N(CH₃)—SO₂—CH₃ | CN | H | F | O |
| (CH₃)₂N— | (CH₃)₂N— | H | —NH—SO₂-n-C₄H₉ | CN | H | F | O |
| (CH₃)₂N— | (CH₃)₂N— | H | —O—SO₂—CH₃ | CN | H | F | O |
| (CH₃)₂N— | (CH₃)₂N— | H | —NH—P(O)(CH₃)(OCH₃) | CN | H | F | O |
| (CH₃)₂N— | (CH₃)₂N— | H | —NH—P(O)(OC₂H₅)₂ | CN | H | F | O |
| (CH₃)₂N— | (CH₃)₂N— | H | —OH | CN | H | F | O |
| (CH₃)₂N— | (CH₃)₂N— | H | —O—CH₃ | CN | H | F | O |
| (CH₃)₂N— | (CH₃)₂N— | H | —O—C₂H₅ | CN | H | F | O |
| (CH₃)₂N— | (CH₃)₂N— | H | —O—CH₂—C≡CH | CN | H | F | O |
| (CH₃)₂N— | (CH₃)₂N— | H | —S—C₂H₅ | CN | H | F | O |
| (CH₃)₂N— | (CH₃)₂N— | H | —O—CH(CH₂F)₂ | CN | H | F | O |
| (CH₃)₂N— | (CH₃)₂N— | H | —(O—CH₂—CH₂)₂—OCH₃ | CN | H | F | O |
| (CH₃)₂N— | (CH₃)₂N— | H | —O—CH(CH₃)—COOCH₃ | CN | H | F | O |
| (CH₃)₂N— | (CH₃)₂N— | H | —O—CH(CH₃)—C≡CH | CN | H | F | O |
| (CH₃)₂N— | (CH₃)₂N— | H | —S—CH₂—COOCH₃ | CN | H | F | O |
| (CH₃)₂N— | (CH₃)₂N— | H | —CH₂—CN | CN | H | F | O |

TABLE 1-continued

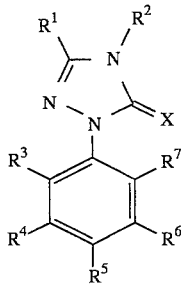

| R¹ | R² | R³ | R⁴ | R⁵ | R⁶ | R⁷ | X |
|---|---|---|---|---|---|---|---|
| (CH₃)₂N— | (CH₃)₂N— | H | 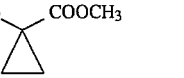 | CN | H | F | O |
| (CH₃)₂N— | (CH₃)₂N— | H | 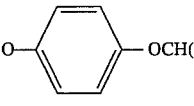 | CN | H | F | O |
| (CH₃)₂N— | (CH₃)₂N— | H | —O—CH₂—Si(CH₃)₃ | CN | H | F | O |
| (CH₃)₂N— | (CH₃)₂N— | H | 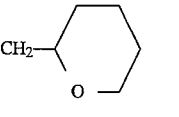 | CN | H | F | O |
| (CH₃)₂N— | (CH₃)₂N— | H | 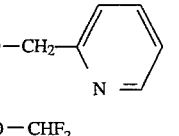 | CN | H | F | O |
| (CH₃)₂N— | (CH₃)₂N— | H | —O—CHF₂ | CN | H | F | O |
| (CH₃)₂N— | (CH₃)₂N— | H | —COOCH₃ | CN | H | Cl | O |
| (CH₃)₂N— | (CH₃)₂N— | H | —CO—NH—CH₃ | CN | H | Cl | O |
| (CH₃)₂N— | (CH₃)₂N— | H | —CO—N(CH₃)₂ | CN | H | F | O |
| (CH₃)₂N— | (CH₃)₂N— | H | —CH₃ | CN | H | F | O |
| (CH₃)₂N— | (CH₃)₂N— | H | Cl | Cl | H | Cl | O |
| (CH₃)₂N— | CH₃—NH— | H | F | NO₂ | H | F | O |
| (CH₃)₂N— | CH₃—NH— | H | F | NO₂ | H | Cl | O |
| (CH₃)₂N— | CH₃—NH— | H | F | CN | H | H | O |
| (CH₃)₂N— | CH₃—NH— | F | H | CN | H | H | O |
| (CH₃)₂N— | CH₃—NH— | Cl | H | CF₃ | H | Cl | O |
| (CH₃)₂N— | CH₃—NH— | Cl | H | Cl | H | H | O |
| (CH₃)₂N— | CH₃—NH— | NO₂ | H | CF₃ | H | NO₂ | O |
| (CH₃)₂N— | CH₃—NH— | Cl | F | CF₃ | H | Cl | O |
| (CH₃)₂N— | CH₃—NH— | H | Cl | CN | Cl | H | O |
| (CH₃)₂N— | CH₃—NH— | H | CN | CN | H | H | O |
| (CH₃)₂N— | CH₃—NH— | Cl | F | NO₂ | H | H | O |
| (CH₃)₂N— | CH₃—NH— | Cl | H | NO₂ | H | Cl | O |
| (CH₃)₂N— | CH₃—NH— | Cl | H | NO₂ | H | F | O |
| (CH₃)₂N— | CH₃—NH— | H | F | CN | H | F | O |
| (CH₃)₂N— | CH₃—NH— | H | F | CN | H | F | S |
| (CH₃)₂N— | CH₃—NH— | H | F | CN | H | Cl | S |
| (CH₃)₂N— | CH₃—NH— | H | F | CN | H | Cl | O |
| (CH₃)₂N— | CH₃—NH— | H | —NH₂ | CN | H | Cl | O |
| (CH₃)₂N— | CH₃—NH— | H | —NH₂ | CN | H | F | O |
| (CH₃)₂N— | CH₃—NH— | H | —NH₂ | CN | H | F | S |
| (CH₃)₂N— | CH₃—NH— | H | —NH—CH₃ | CN | H | F | O |
| (CH₃)₂N— | CH₃—NH— | H | —NH—CH₂—CH=CH₂ | CN | H | F | O |
| (CH₃)₂N— | CH₃—NH— | H | —NH-s-C₄H₉ | CN | H | F | O |
| (CH₃)₂N— | CH₃—NH— | H | —N(CH₃)₂ | CN | H | F | O |
| (CH₃)₂N— | CH₃—NH— | H | —N(CH₂CN)₂ | CN | H | F | O |
| (CH₃)₂N— | CH₃—NH— | H | —NH—SO₂—CH₃ | CN | H | F | O |
| (CH₃)₂N— | CH₃—NH— | H | —NH—SO₂—CH₃ | CN | H | Cl | O |
| (CH₃)₂N— | CH₃—NH— | H | —N(CH₃)—SO₂—CH₃ | CN | H | F | O |
| (CH₃)₂N— | CH₃—NH— | H | —NH—SO₂-n-C₄H₉ | CN | H | F | O |
| (CH₃)₂N— | CH₃—NH— | H | —O—SO₂—CH₃ | CN | H | F | O |
| (CH₃)₂N— | CH₃—NH— | H | —NH—P(O)(CH₃)(OCH₃) | CN | H | F | O |
| (CH₃)₂N— | CH₃—NH— | H | —NH—P(O)(OC₂H₅)₂ | CN | H | F | O |
| (CH₃)₂N— | CH₃—NH— | H | —OH | Cl | H | F | O |
| (CH₃)₂N— | CH₃—NH— | H | —O—CH₃ | CN | H | F | O |

TABLE 1-continued

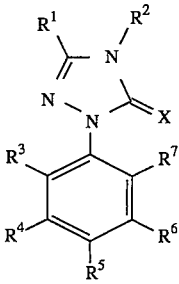

| R¹ | R² | R³ | R⁴ | R⁵ | R⁶ | R⁷ | X |
|---|---|---|---|---|---|---|---|
| $(CH_3)_2N-$ | $CH_3-NH-$ | H | $-O-C_2H_5$ | CN | H | F | O |
| $(CH_3)_2N-$ | $CH_3-NH-$ | H | $-O-CH_2-C\equiv CH$ | CN | H | F | O |
| $(CH_3)_2N-$ | $CH_3-NH-$ | H | $-S-C_2H_5$ | CN | H | F | O |
| $(CH_3)_2N-$ | $CH_3-NH-$ | H | $-O-CH(CH_2F)_2$ | CN | H | F | O |
| $(CH_3)_2N-$ | $CH_3-NH-$ | H | $-(O-CH_2-CH_2)_2-OCH_3$ | CN | H | F | O |
| $(CH_3)_2N-$ | $CH_3-NH-$ | H | $-O-CH(CH_3)-COOCH_3$ | CN | H | F | O |
| $(CH_3)_2N-$ | $CH_3-NH-$ | H | $-O-CH(CH_3)-C\equiv CH$ | CN | H | F | O |
| $(CH_3)_2N-$ | $CH_3-NH-$ | H | $-S-CH_2-COOCH_3$ | CN | H | F | O |
| $(CH_3)_2N-$ | $CH_3-NH-$ | H | $-CH_2-CN$ | CN | H | F | O |
| $(CH_3)_2N-$ | $CH_3-NH-$ | H | 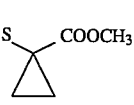 | CN | H | F | O |
| $(CH_3)_2N-$ | $CH_3-NH-$ | H | 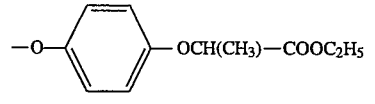 | CN | H | F | O |
| $(CH_3)_2N-$ | $CH_3-NH-$ | H | $-O-CH_2-Si(CH_3)_3$ | CN | H | F | O |
| $(CH_3)_2N-$ | $CH_3-NH-$ | H | 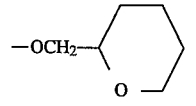 | CN | H | F | O |
| $(CH_3)_2N-$ | $CH_3-NH-$ | H | 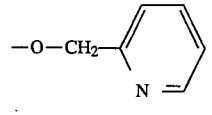 | CN | H | F | O |
| $(CH_3)_2N-$ | $CH_3-NH-$ | H | $-O-CHF_2$ | CN | H | F | O |
| $(CH_3)_2N-$ | $CH_3-NH-$ | H | $-COOCH_3$ | CN | H | Cl | O |
| $(CH_3)_2N-$ | $CH_3-NH-$ | H | $-CO-NH-CH_3$ | CN | H | Cl | O |
| $(CH_3)_2N-$ | $CH_3-NH-$ | H | $-CO-N(CH_3)_2$ | CN | H | F | O |
| $(CH_3)_2N-$ | $CH_3-NH-$ | H | $-CH_3$ | CN | H | F | O |
| $(CH_3)_2N-$ | $CH_3-NH-$ | H | Cl | Cl | H | Cl | O |
| $(CH_3)_2N-$ | $F_2CH-$ | H | F | $NO_2$ | H | F | O |
| $(CH_3)_2N-$ | $F_2CH-$ | H | F | $NO_2$ | H | Cl | O |
| $(CH_3)_2N-$ | $F_2CH-$ | H | F | CN | H | H | O |
| $(CH_3)_2N-$ | $F_2CH-$ | F | H | CN | H | H | O |
| $(CH_3)_2N-$ | $F_2CH-$ | Cl | H | $CF_3$ | H | Cl | O |
| $(CH_3)_2N-$ | $F_2CH-$ | Cl | H | Cl | H | H | O |
| $(CH_3)_2N-$ | $F_2CH-$ | $NO_2$ | H | $CF_3$ | H | $NO_2$ | O |
| $(CH_3)_2N-$ | $F_2CH-$ | Cl | F | $CF_3$ | H | Cl | O |
| $(CH_3)_2N-$ | $F_2CH-$ | H | Cl | CN | Cl | H | O |
| $(CH_3)_2N-$ | $F_2CH-$ | H | CN | CN | H | H | O |
| $(CH_3)_2N-$ | $F_2CH-$ | Cl | F | $NO_2$ | H | H | O |
| $(CH_3)_2N-$ | $F_2CH-$ | Cl | H | $NO_2$ | H | Cl | O |
| $(CH_3)_2N-$ | $F_2CH-$ | Cl | H | $NO_2$ | H | F | O |
| $(CH_3)_2N-$ | $F_2CH-$ | H | F | CN | H | F | O |
| $(CH_3)_2N-$ | $F_2CH-$ | H | F | CN | H | F | S |
| $(CH_3)_2N-$ | $F_2CH-$ | H | F | CN | H | Cl | S |
| $(CH_3)_2N-$ | $F_2CH-$ | H | F | CN | H | Cl | O |
| $(CH_3)_2N-$ | $F_2CH-$ | H | $NH_2$ | CN | H | Cl | O |
| $(CH_3)_2N-$ | $F_2CH-$ | H | $-NH_2$ | CN | H | Cl | O |
| $(CH_3)_2N-$ | $F_2CH-$ | H | $-NH_2$ | CN | H | F | O |
| $(CH_3)_2N-$ | $F_2CH-$ | H | $-NH_2$ | CN | H | F | S |
| $(CH_3)_2N-$ | $F_2CH-$ | H | $-NH-CH_3$ | CN | H | F | O |
| $(CH_3)_2N-$ | $F_2CH-$ | H | $-NH-CH_2-CH=CH_2$ | CN | H | F | O |

TABLE 1-continued

| R¹ | R² | R³ | R⁴ | R⁵ | R⁶ | R⁷ | X |
|---|---|---|---|---|---|---|---|
| $(CH_3)_2N-$ | $F_2CH-$ | H | $-NH-s-C_4H_9$ | CN | H | F | O |
| $(CH_3)_2N-$ | $F_2CH-$ | H | $-N(CH_3)_2$ | CN | H | F | O |
| $(CH_3)_2N-$ | $F_2CH-$ | H | $-N(CH_2CN)_2$ | CN | H | F | O |
| $(CH_3)_2N-$ | $F_2CH-$ | H | $-NH-SO_2-CH_3$ | CN | H | F | O |
| $(CH_3)_2N-$ | $F_2CH-$ | H | $-NH-SO_2-CH_3$ | CN | H | O | O |
| $(CH_3)_2N-$ | $F_2CH-$ | H | $-N(CH_3)-SO_2-CH_3$ | CN | H | F | O |
| $(CH_3)_2N-$ | $F_2CH-$ | H | $-NH-SO_2-n-C_4H_9$ | CN | H | F | O |
| $(CH_3)_2N-$ | $F_2CH-$ | H | $-O-SO_2-CH_3$ | CN | H | F | O |
| $(CH_3)_2N-$ | $F_2CH-$ | H | $-NH-P(O)(CH_3)(OCH_3)$ | CN | H | F | O |
| $(CH_3)_2N-$ | $F_2CH-$ | H | $-NH-P(O)(OC_2H_5)_2$ | CN | H | F | O |
| $(CH_3)_2N-$ | $F_2CH-$ | H | $-OH$ | CN | H | F | O |
| $(CH_3)_2N-$ | $F_2CH-$ | H | $-O-CH_3$ | CN | H | F | O |
| $(CH_3)_2N-$ | $F_2CH-$ | H | $-O-C_2H_5$ | CN | H | F | O |
| $(CH_3)_2N-$ | $F_2CH-$ | H | $-O-CH_2-C\equiv CH$ | CN | H | F | O |
| $(CH_3)_2N-$ | $F_2CH-$ | H | $-S-C_2H_5$ | CN | H | F | O |
| $(CH_3)_2N-$ | $F_2CH-$ | H | $-O-CH(CH_2F)_2$ | CN | H | F | O |
| $(CH_3)_2N-$ | $F_2CH-$ | H | $-(O-CH_2-CH_2)_2-OCH_3$ | CN | H | F | O |
| $(CH_3)_2N-$ | $F_2CH-$ | H | $-O-CH(CH_3)-COOCH_3$ | CN | H | F | O |
| $(CH_3)_2N-$ | $F_2CH-$ | H | $-O-CH(CH_3)-C\equiv CH$ | CN | H | F | O |
| $(CH_3)_2N-$ | $F_2CH-$ | H | $-S-CH_2-COOCH_3$ | CN | H | F | O |
| $(CH_3)_2N-$ | $F_2CH-$ | H | $-CH_2-CN$ | CN | H | F | O |
| $(CH_3)_2N-$ | $F_2CH-$ | H | $-S-\text{cyclopropyl}-COOCH_3$ | CN | H | F | O |
| $(CH_3)_2N-$ | $F_2CH-$ | H | $-O-C_6H_4-OCH(CH_3)-COOC_2H_5$ | CN | H | F | O |
| $(CH_3)_2N-$ | $F_2CH-$ | H | $-O-CH_2-Si(CH_3)_3$ | CN | H | F | O |
| $(CH_3)_2N-$ | $F_2CH-$ | H | $-OCH_2-\text{(tetrahydropyranyl)}$ | CN | H | F | O |
| $(CH_3)_2N-$ | $F_2CH-$ | H | $-O-CH_2-\text{(pyridyl)}$ | CN | H | F | O |
| $(CH_3)_2N-$ | $F_2CH-$ | H | $-O-CHF_2$ | CN | H | F | O |
| $(CH_3)_2N-$ | $F_2CH-$ | H | $-COOCH_3$ | CN | H | O | O |
| $(CH_3)_2N-$ | $F_2CH-$ | H | $-CO-NH-CH_3$ | CN | H | Cl | O |
| $(CH_3)_2N-$ | $F_2CH-$ | H | $-CO-N(CH_3)_2$ | CN | H | F | O |
| $(CH_3)_2N-$ | $F_2CH-$ | H | $-CH_3$ | CN | H | F | O |
| $(CH_3)_2N-$ | $F_2CH-$ | H | Cl | Cl | H | Cl | O |

Using, for example, 4-methyl-3-dimethylamino-1,2,4-triazolin-5-one and 2,4,5-trifluorobenzonitrile as starting materials, the reaction sequence of process (a) according to the invention can be represented by the following formula scheme:

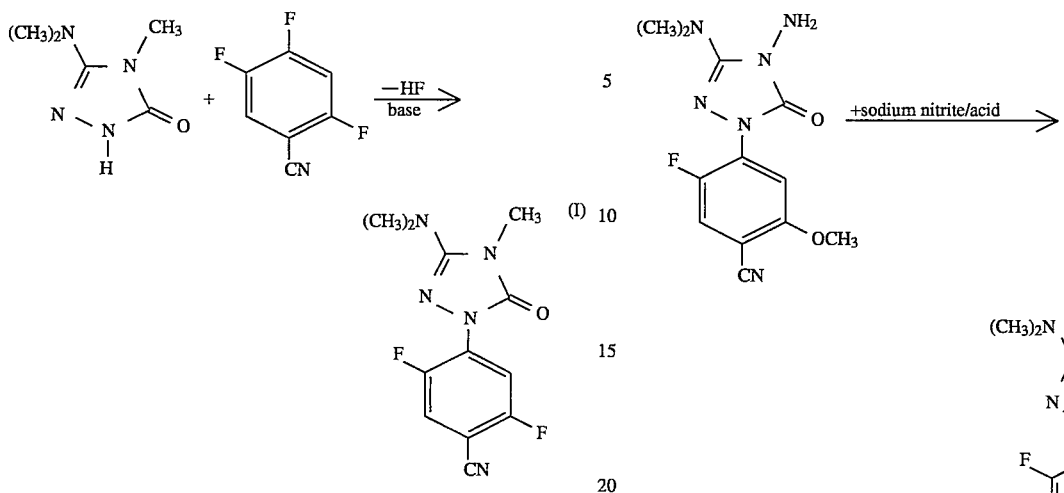

Using, for example, 1-(4-cyano-2,5-difluorophenyl)-4-methyl-3-dimethylamino-1,2,4-triazolin-5-one and 1-butin-3-ol as starting materials, the reaction sequence of process (b) according to the invention can be represented by the following formula scheme:

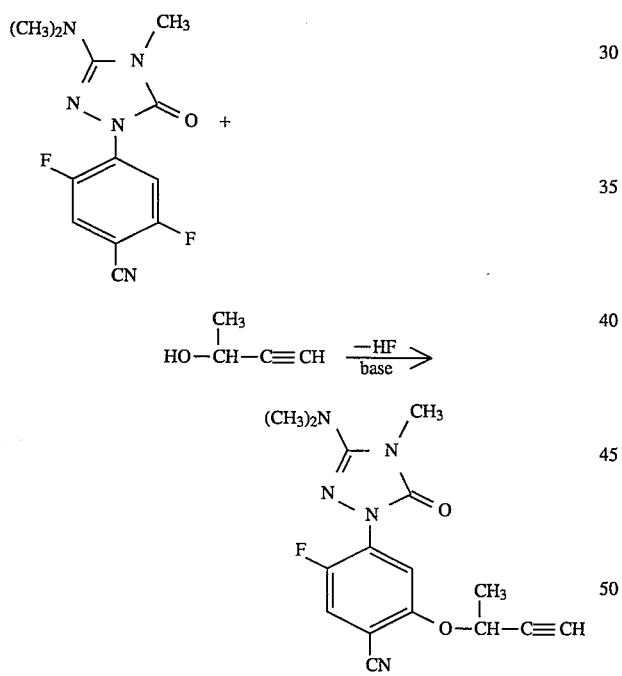

Using, for example, 1-(4-cyano-2-fluoro-5-methoxyphenyl)-4-amino-3-dimethyamino-1,2,4-triazolin-5-one and sodium nitrite as starting materials, the reaction sequence of process (c) according to the invention can be represented by the following formula scheme:

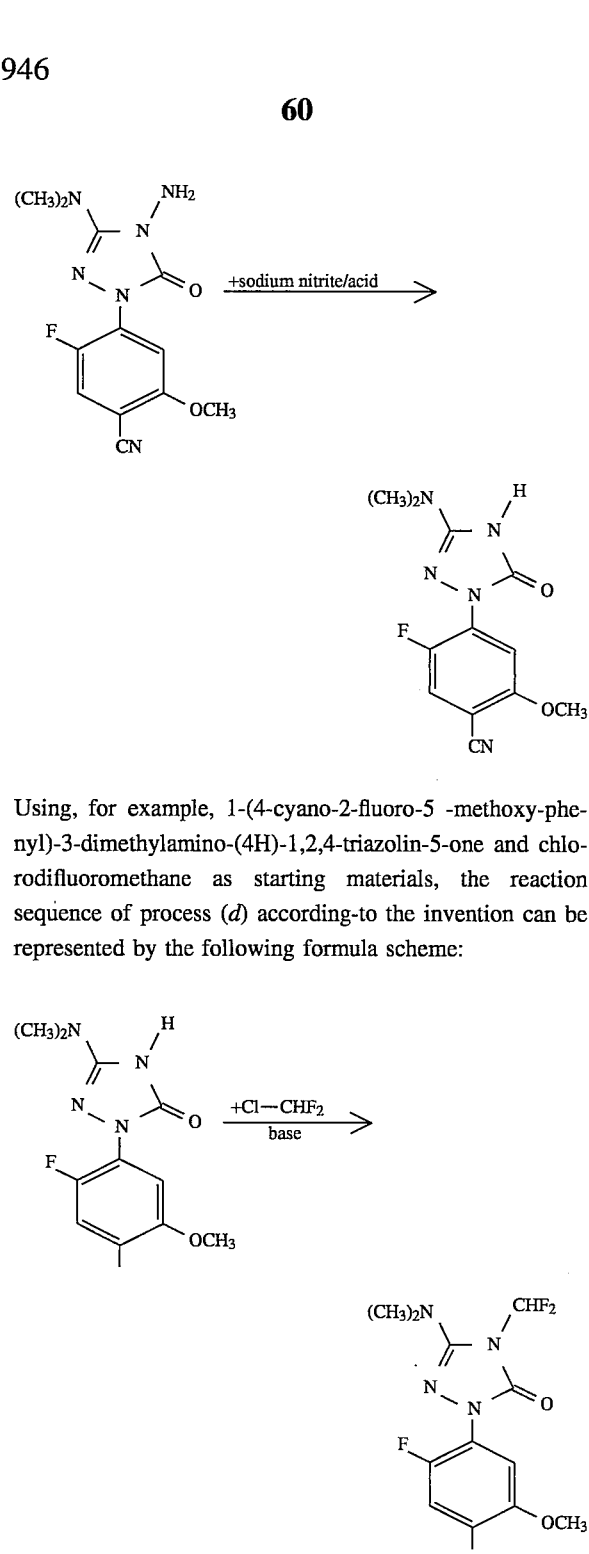

Using, for example, 1-(4-cyano-2-fluoro-5-methoxy-phenyl)-3-dimethylamino-(4H)-1,2,4-triazolin-5-one and chlorodifluoromethane as starting materials, the reaction sequence of process (d) according-to the invention can be represented by the following formula scheme:

Using, for example, 2,6-dichloro-4-trifluoromethylphenylhydrazine and chlorotrimethylformamidiniumhydrochloride as starting materials, the reaction sequence of process (e) according to the invention can be represented by the following formula scheme:

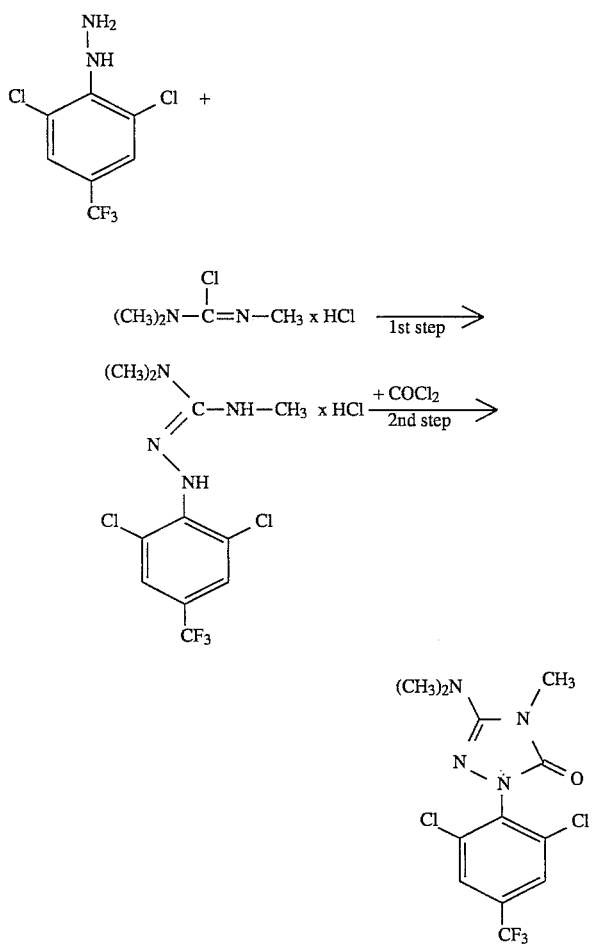

A general definition of the 1H-triazolinones required as starting materials for carrying out process (a) according to the invention is given by the formula (II). In this formula (II), $R^1$, $R^2$ and X preferably and particularly preferably represent those radicals already mentioned as preferred and particularly preferred for these substituents in connection with the description of the compounds of the formula (I) according to the invention. The 1H-triazolinones of the formula (II) are known or are obtainable by analogy with known processes (cf. e.g. EP 283 876; EP 305 844; EP 513 621; EP 415 196; Chem. Ber. 102, 755–766 [1969]; Liebigs Ann. Chem. 343, 24 [1905]). Furthermore, 1H-triazolinones of the formula (II) are obtained by a previously unknown process when chloro-formamidiniumhydrochlorides of the formula (VI),

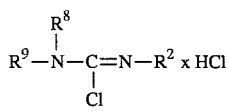 (VI)

in which $R^2$, $R^8$ and $R^9$ have the definitions given above, are reacted with carbazates of the formula (IX),

 (IX)

in which $R^1$ has the definition given above, optionally in the presence of a diluent such as, for example, acetonitrile and optionally in the presence of a reaction auxiliary such as, for example, sodium hydrogen carbonate at temperatures of between –20° C. and +100° C. (compare also in this respect the Preparation Examples).

A general definition of the halogenobenzene derivatives also required as starting materials for carrying out process (a) according to the invention is given by the formula (III). In this formula (III), $R^3$, $R^4$, $R^5$, $R^6$ and $R^7$ preferably and particularly preferably represent those radicals already mentioned as preferred and particularly preferred for these substituents in connection with the description of the compounds of the formula (I) according to the invention. $Hal^1$ represents preferably fluorine, chlorine or bromine and in particular fluorine or chlorine.

The halogenobenzene derivatives of the formula (III) are generally known or are obtainable by analogy with known processes (cf. e.g. EP 191 181; EP 441 004; EP 431 373). Previously unknown is the compound 5-chloro-2,4-difluorobenzonitrile. It is obtained when the known compound 2,4,5-trichlorobenzonitrile (cf. e.g. EP 441 004) is reacted with potassium fluoride, optionally in the presence of a diluent such as, for example, tetramethylenesulphone, at temperatures of between 100° C. and 200° C. (compare also in this respect the Preparation Examples).

A general definition of the substituted triazolinones required as starting compound for carrying out process (b) according to the invention is given by the formula (Ia). In this formula (Ia), $R^1$, $R^2$, $R^3$, $R^5$ $R^6$ $R^7$ and X preferably and particularly preferably represent those radicals already mentioned as preferred and particularly preferred for these substituents in connection with the description of the substances of the formula (I) according to the invention. $Hal^2$ represents preferably fluorine, chlorine or bromine and in particular fluorine or chlorine.

The substituted triazolinones of the formula (Ia) are compounds in accordance with the invention and are obtainable by using processes (a), (c), (d) and/or (e) according to the invention.

A general definition of the nucleophiles also required as starting compounds for carrying out process (b) according to the invention is given by the formula (IV). In this formula (IV), $R^{13}$ preferably represents a radical of the formula —O—$R^{12}$, —S—$R^{12}$ or —$NR^{11}R^{12}$, where $R^{11}$ and $R^{12}$ preferably represent those radicals already mentioned as preferred and particularly preferred for these substituents in connection with the description of the substances of the formula (I) according to the invention.

The nucleophiles of the formula (IV) are generally known compounds of organic chemistry.

A general definition of the substituted triazolinones required as starting compounds for carrying out process (c) according to the invention is given by the formula (Ib). In this formula (Ib), $R^1$, $R^3$, $R^4$, $R^5$, $R^6$, $R^7$ and X preferably and particularly preferably represent those radicals already mentioned as preferred and particularly preferred for these substituents in connection with the description of the substances of the formula (I) according to the invention.

The substituted triazolinones of the formula (Ib) are compounds in accordance with the invention and are obtainable by using processes (a), (b) and/or (e) according to the invention.

A general definition of the substituted triazolinones required as starting compounds for carrying out process (d) according to the invention is given by the formula (Ic). In this formula (Ic), $R^1$, $R^3$, $R^4$, $R^5$, $R^6$, $R^7$ and X preferably and particularly preferably represent those radicals already mentioned as preferred and particularly preferred for these substituents in connection with the description of the substances of the formula (I) according to the invention.

The substituted triazolinones of the formula (Ic) are compounds in accordance with the invention and are obtainable by using processes (a), (b), (c) and/or (e) according to the invention.

A general definition of the alkylating agents also required as starting compounds for carrying out process (d) according to the invention is given by the formula (V). In this formula (V), $R^{2-1}$ preferably and particularly preferably represents those radicals already mentioned as preferred and particularly preferred for the substituent $R^{10}$ in connection with the description of the substances of the formula (I) according to the invention, with the exception of the optionally substituted aryl and heterocyclyl radicals. $E^1$ preferably represents a leaving radical which is customary in alkylating agents, for example halogen, and in particular represents chlorine, bromine or iodine, or represents in each case optionally substituted alkylsulphonyloxy, alkoxysulphonyloxy or arylsulphonyloxy, such as, in particular methanesulphonyloxy, trifluoromethanesulphonyloxy, methoxysulphonyloxy, ethoxysulphonyloxy or p-toluenesulphonyloxy.

The alkylating agents of the formula (V) are generally known compounds of organic chemistry.

A general definition of the chloro-formamidinium hydrochlorides required as starting compounds for carrying out process (e) according to the invention is given by the formula (VI). In this formula (VI), $R^2$, $R^8$ and $R^9$ preferably and particularly preferably represent those radicals already mentioned as preferred and particularly preferred for these substituents in connection with the description of the substances of the formula (I) according to the invention. The chloro-formamidiniumhydrochlorides of the formula (VI) are known or are obtainable by analogy with known processes (cf. e.g. EP 283 876; EP 398 097; *Chem. Bet.* 97, 1232 [1964]).

A general definition of the arylhydrazines also required as starting compounds for carrying out process (e) according to the invention is given by the formula (VII). In this formula (VII), $R^3$, $R^4$, $R^5$, $R^6$ and $R^7$ preferably and particularly preferably represent those radicals already mentioned as preferred and particularly preferred for these substituents in connection with the description of the substances of the formula (I) according to the invention The arylhydrazines of the formula (VII) are generally known compounds of organic chemistry, or are obtainable by analogy with known processes (cf. e.g. Houben-Weyl "Methoden der organischen Chemic", *Thieme Verlag Stuttgart*, Volume X/2, pp. 180, 201, 245; *Angew. Chem.* 80, 284 [1968]; *Chem. Ber.* 102, 3088 [1969]; DE 33 37 543; DE 34 02 308; DE 34 47 211; DE 39 03 799).

Suitable diluents for carrying out process (a) according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, or esters, such as methyl acetate or ethyl acetate.

Process (a) according to the invention is preferably carried out in the presence of a suitable reaction auxiliary. Suitable such auxiliaries are all conventional inorganic or organic bases. These include, for example, alkaline earth metal or alkali metal hydroxides, such as sodium hydroxide, calcium hydroxide, potassium hydroxide or else ammonium hydroxide, alkali metal carbonates, such as sodium carbonate, potassium carbonate, potassium hydrogen carbonate, sodium hydrogen carbonate or ammonium carbonate, alkali metal or alkaline earth metal acetates, such as sodium acetate, potassium acetate, calcium acetate or ammonium acetate, and tertiary amines, such as trimethylamine, triethylamine, tributylamine, N,N-dimethylaniline, pyridine, piperidine, N-methylpiperidine, N,N-dimethylaminopyridine, diazabicyclooctane (DABCO), diazabicyclononene (DBN) or diazabicycloundecene (DBU).

When carrying out process (a) according to the invention, the reaction temperatures can be varied over a wide range. In general it is carried out at temperatures of between 0° C. and +180° C., preferably at temperatures of between +20° C. and +120° C.

Process (a) according to the invention is usually carried out under atmospheric pressure. It is however also possible to work under elevated or reduced pressure.

To carry out process (a) according to the invention requires the use, per mole of 1H-triazolinone of the formula (II), of in general 1.0 to 3.0 mol, preferably 1.0 to 1.5 mol, of halogenobenzene derivative of the formula (III) and optionally 1.0 to 3.0 mol, preferably 1.0 to 1.5 mol, of base as reaction auxiliary. The reaction procedure, work-up and isolation of the reaction products are carried out by known processes which are generally conventional (compare also the Preparation Examples).

Suitable diluents for carrying out process (b) according to the invention are inert organic solvents. It is preferred to use the solvents listed in the description of the procedure of process (a) according to the invention.

Process (b) according to the invention is preferably carried out in the presence of a suitable reaction auxiliary. Suitable such auxiliaries are all conventional inorganic or organic bases. These include, for example, alkaline earth metal or alkali metal hydrides, hydroxides, amides, alcoholates, acetates, carbonates or hydrogen carbonates, such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out process (b) according to the invention, the reaction temperatures can be varied over a wide range. In general it is carried out at temperatures of between −20° C. and +150° C., preferably at temperatures of between 0° C. and +120° C.

Process (b) according to the invention is usually carried out under atmospheric pressure. It is however also possible to work under elevated or reduced pressure.

To carry out process (b) according to the invention requires the use, per mole of substituted triazolinone of the formula (Ia), of in general 1.0 to 3.0 mol, preferably 1.0 to 1.5 mol, of nucleophile of the formula (IV) and optionally 0.1 to 3.0 mol, preferably 1.0 to 1.5 mol, of base as reaction auxiliary.

The reaction procedure, work-up and isolation of the reaction products are carried out by known processes which are generally conventional (cf. also the Preparation Examples).

Process (c) according to the invention is usually carried out in the presence of a suitable acid. Suitable such acids are, in particular, aqueous mineral acids, It is particularly preferred to use dilute hydrochloric acid.

Suitable diluents for carrying out process (c) according to the invention are all diluents which are conventional for such diazotization reactions. It is particularly preferred to use the aqueous mineral acids, such as, for example, hydrochloric acid, which are employed as reagents simultaneously as diluents, in appropriate excess.

When carrying out process (c) according to the invention, the reaction temperatures can be varied over a wide range. In general it is carried out at temperatures of between −20° C. and +100° C., preferably at temperatures of between −10° C. and +80° C.

Process (c) according to the invention is usually carried out under atmospheric pressure. It is however also possible to work under elevated or reduced pressure.

To carry out process (c) according to the invention requires the use, per mole of substituted triazolinone of the formula (Ib), of in general 1.0 to 3.0 mol, preferably 1.0 to 2.0 mol, of sodium nitrite and 1.0 to 10.0 mol, preferably 1.0 to 5.0 mol, of acid.

The reaction procedure, work-up and isolation of the reaction products are carried out by known processes which are generally conventional (compare also the Preparation Examples).

Suitable diluents for carrying out process (d) according to the invention are inert organic solvents. These include, in particular, aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide; esters such as methyl acetate or ethyl acetate, or sulphoxides, such as dimethyl sulphoxide.

Process (d) according to the invention can optionally also be carried out in a two-phase system, such as, for example, water/toluene or water/dichloromethane, optionally in the presence of a suitable phase-transfer catalyst. Examples of such catalysts which may be mentioned are: tetrabutylammonium iodide, tetrabutylammonium bromide, tetrabutylammonium chloride, tributyl-methylphosphonium bromide, trimethyl-$C_{13}$/$C_{15}$-alkylammonium chloride, trimethyl-$C_{13}$/$C_{15}$-alkylammonium bromide, dibenzyl-dimethyl-ammonium methylsulphate, dimethyl-$C_{12}$/$C_{14}$-alkyl-benzylammonium chloride, dimethyl-$C_{12}$/$C_{14}$-alkyl-benzylammonium bromide, tetrabutylammonium hydroxide, triethylbenzylammonium chloride, methyltrioctylammonium chloride, trimethylbenzylammonium chloride, 15-crown-5, 18-crown-6 or tris-[2-(2-methoxyethoxy)-ethyl]-amine.

Process (d) according to the invention is preferably carried out in the presence of a suitable reaction auxiliary. Suitable such auxiliaries are all conventional inorganic or organic bases. These include, for example, alkaline earth metal or alkali metal hydrides, hydroxides, amides, alcoholates, acetates, carbonates or hydrogen carbonates, such as, for example, sodium hydride, sodium amide, sodium methylate, sodium ethylate, potassium tert.-butylate, sodium hydroxide, potassium hydroxide, ammonium hydroxide, sodium acetate, potassium acetate, calcium acetate, ammonium acetate, sodium carbonate, potassium carbonate, potassium hydrogen carbonate, sodium hydrogen carbonate or ammonium carbonate, and tertiary amines, such as trimethylamine, triethylamine, tributylamine, N,N-dimethylaniline, pyridine, N-methylpiperidine, N,N-dimethylaminopyridine, diazabicyclooctane (DABCO), diazabicyclononene (DBN) or diazabicycloundecene (DBU).

When carrying out process (d) according to the invention, the reaction temperatures can be varied over a wide range. In general it is carried out at temperatures of between −20° C. and +150° C., preferably at temperatures of between 0° C. and +120° C.

Process (d) according to the invention is usually carried out under atmospheric pressure. It is however also possible to work under elevated or reduced pressure.

To carry out process (d) according to the invention requires the use, per mole of substituted triazolinone of the formula (Ic), of in general 1.0 to 3.0 mol, preferably 1.0 to 2.0 mol, of alkylating agent of the formula (V) and optionally 1.0 to 3.0 mol, preferably 1.0 to 2.0 mol, of base as reaction auxiliary.

The reaction procedure, work-up and isolation of the reaction products are carried out in both cases by known processes which are generally conventional (compare also the Preparation Examples).

Suitable diluents for carrying out the 1st stage of process (e) according to the invention are inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, esters, such as methyl acetate or ethyl acetate, or alcohols, such as methanol, ethanol, propanol or butanol.

When carrying out the 1st stage of process (e) according to the invention, the reaction temperatures can be varied over a wide range. In general it is carried out at temperatures of between −20° C. and +100° C., preferably at temperatures of between 0° C. and +80° C.

The 1st stage of process (e) according to the invention is usually carried out under atmospheric pressure. It is however also possible to work under elevated or reduced pressure.

To carry out the 1st stage of process (e) according to the invention requires the use, per mole of chloroformamidinium hydrochloride of the formula (VI), of in general 0.1 to 1.0 mol, preferably 0.4 to 0.6 mol, of arylhydrazine of the formula (VIII). The reaction procedure, work-up and isolation of the reaction products are carried out by known processes which are generally conventional (compare in this respect also the Preparation Examples).

Suitable diluents for carrying out the 2nd stage of process (e) according to the invention are likewise inert organic solvents. These include, in particular, aliphatic, alicyclic or aromatic, optionally halogenated hydrocarbons such as, for example, benzine, benzene, toluene, xylene, chlorobenzene, dichlorobenzene, petroleum ether, hexane, cyclohexane, dichloromethane, chloroform or carbon tetrachloride; ethers, such as diethyl ether, diisopropyl ether, dioxane, tetrahydrofuran or ethylene glycol dimethyl or diethyl ether; ketones, such as acetone, butanone or methyl isobutyl ketone; nitriles, such as acetonitrile, propionitrile or benzonitrile; amides, such as N,N-dimethylformamide, N,N-dimethylacetamide, N-methylformanilide, N-methylpyrrolidone or hexamethylphosphoric triamide, or esters, such as methyl acetate or ethyl acetate.

When carrying out the 2nd stage of process (e) according to the invention, the reaction temperatures can be varied over a wide range. In general it is carried out at temperatures of between −20° C. and +100° C., preferably at temperatures of between 0° C. and +80° C.

The 2nd stage of process (e) according to the invention is usually carried out under atmospheric pressure. It is however also possible to work under elevated or reduced pressure.

To carry out the 2nd stage of process (e) according to the invention requires the use, per mole of the intermediate of the formula (VIII), of in general 2.0 to 20.0 mol, preferably 10.0 to 15.0 mol of phosgene. The reaction procedure, work-up and isolation of the reaction products are carried out by known processes which are generally conventional (compare also in this respect the Preparation Examples).

The purification of the end products of the formula (I) is carried out by using conventional processes, for example by column chromatography, or by recrystallization.

The products are characterized by their melting point or, in the case of non-crystallizing compounds, by using proton nuclear magnetic resonance spectroscopy ($^1$H—NMR).

The active compounds according to the invention can be used as defoliants, desiccants, agents for destroying broad-leaved plants and, especially, as weed-killers. By weeds, in the broadest sense, there are to be understood all plants which grow in locations where they are not wanted. Whether the substances according to the invention act as total or selective herbicides depends essentially on the amount used.

The active compounds according to the invention can be used, for example, in connection with the following plants:

Dicotyledon weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsium, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledon cultures of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledon weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledon cultures of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

The compounds are suitable, depending on the concentration, for the total combating of weeds, for example on industrial terrain and rail tracks, and on paths and squares with or without trees planted. Equally, the compounds can be employed for combating weeds in perennial cultures, for example forests, decorative tree plantings, orchards, vineyards, citrus groves, nut orchards, banana plantations, coffee plantations, tea plantations, rubber plantations, oil palm plantations, cocoa plantations, soft fruit plantings and hopfields, and for the selective combating of weeds in annual cultures.

In this context, the active compounds according to the invention can be employed with particularly high success for combating dicotyledon weeds in monocotyledon cultures such as, for example, wheat or maize. In addition, the active compounds according to the invention also possess, at appropriate application rates, foliar-insecticidal and acaridical activity.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, and furthermore in formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents, liquefied gases under pressure, and/or solid carriers, optionally with the use of surface-active agents, that is emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example ligninsulphite waste liquors and methylcellulose.

Adhesives such as carboxymethylcellulose and natural and Synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

For combating weeds, the active compounds according to the invention, as such or in the form of their formulations, can also be used as mixtures with known herbicides, finished formulations or tank mixes being possible.

Possible components for the mixtures are known herbicides, for example anilides, such as diflufenican and propanil; arylcarboxylic acids, such as dichloropicolinic acid, dicamba or picloram; aryloxyalkanoic acids, such as 2,4-D, 2,4-DB, 2,4-DP, fluroxypyr, MCPA, MCPP and triclopyr; aryloxy-phenoxy-alkanoates, such as diclofopmethyl, fenoxaprop-ethyl, fluazifop-butyl, haloxyfopmethyl and quizalofop-ethyl; azinones, such as chloridazon and norflurazon; carbamates, such as chlorpropham, desmedipham, phenmedipham and propham; chloroacetanilides, such as alachlor, acetochlor, butachlor, metazachlor, metolachlor, pretilachlor and propachlor; dinitroanilines, such as oryzalin, pendimethalin and trifluralin; diphenyl ethers, such as acifluorfen, bifenox, fluoroglycofen, fomesafen, halosafen, lactofen and oxyfluorfen; ureas, such as chlortoluron, diuron, fluometuron, isoproturon, linuron and methabenzthiazuron; hydroxylamines, such as alloxydim, clethodim, cycloxydim, sethoxydim and tralkoxydim; imidazolinones, such as imazethapyr, imazamethabenz, imazapyr and imazaquin; nitriles, such as bromoxynil, dichlobenil and ioxynil; oxyacetamides, such as mefenacet; sulphonylureas, such as amidosulfuron, bensulfuron-methyl, chlorimuron-ethyl, chlorsulfuron, cinosulfuron, metsulfuron-methyl, nicosulfuron, primisulfuron, pyrazosulfuron-ethyl, thifensulfuronmethyl, triasulfuron and tribehuronmethyl; thiocarbamates, such as butylate, cycloate, diallate, EPTC, esprocarb, molinate, prosulfocarb, thiobencarb and triallate; triazines, such as atrazin, cyanazin, simazin, simetryne, terbutryne and terbutylazin; triazinones such as hexazinon, metamitron and metribuzin; and others, such as aminotriazole, benfuresate, bentazone, cimethylin, clomazone, clopyralid, difenzoquat, dithiopyr, ethofumesate, fluorochloridone, glufosinate, glyphosate, isoxaben, pyridate, quinchlorac, quinmerac, sulphosate and tridiphane.

Mixtures with other known active compounds, such as fungicides, insecticides, acaricides, nematicides, bird repellents, plant nutrients and agents which improve soil structure, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by watering, spraying; atomizing or scattering.

The active compounds according to the invention can be applied either before or after emergence of the plants. They can also be incorporated into the soil before sowing.

The amount of active compound used can vary within a wide range. It depends essentially on the nature of the desired effect. In general, the amounts used are between 0.01 and 10 kg of active compound per hectare of soil surface, preferably between 0.05 and 5 kg per hectare.

The preparation and use of the active compounds according to the invention can be seen from the following examples.

PREPARATION EXAMPLES

EXAMPLE 1

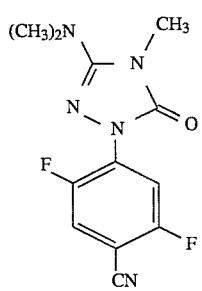

(process a) 7.1 g (0.05 mol) of 3-dimethylamino-4-methyl-1 H-1,2,4-triazolin-5-one (cf. e.g. EP 283 876) and 7.85 g (0.05 mol) of 2,4,5-trifluorobenzonitrile (cf. EP 191 181) in 100 ml of dimethyl sulphoxide are admixed at room temperature with 8.3 g (0.06 mol) of potassium carbonate, and the mixture is then stirred for one hour at 80° C. to 90° C. For working up, the reaction mixture is cooled and placed in 300 ml of water, and the solid which is precipitated out is filtered off, washed with water and dried.

9.3 g (67% of theory) of 1-(4-cyano-2,5-difluorophenyl)-4-methyl-3-dimethylamino-1,2,4-triazolin-5-one are obtained with a melting point of 131°–133° C.

EXAMPLE 2

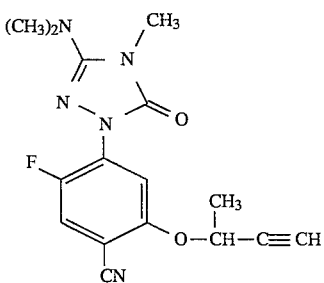

Process b 0.24 g (0.006 mol) of sodium hydride (60% in paraffin oil) is added at room temperature to 0.42 g (0.006 mol) of 3-butin-1-ol in 50 ml of acetonitrile, the mixture is stirred for 10 minutes at room temperature and then 1.2 g (0.0043 mol) of 1-(4-cyano-2,5-difluorophenyl)-4 -methyl-3-dimethylamino-1,2,4-triazolin-5-one is added, and the mixture is stirred for a further 2 hours at room temperature. For working up, the reaction mixture is filtered, the filtrate is concentrated in vacuo, the residue is partitioned between dichloromethane and water, the organic phase is separated off and dried over sodium sulphate, concentrated in vacuo and crystallization is induced by stirring it with a little methanol.

0.7 g (50% of theory) of 1-(4-cyano-2-fluoro-5-but-1-in-3-yl-oxy-phenyl)-4-methyl-3-dimethylamino-1,2,4-triazolin-5-one are obtained with a melting point of 112°–114° C.

EXAMPLE 3

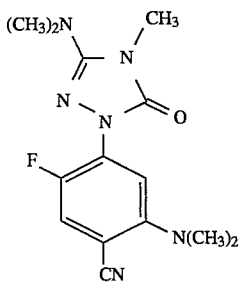

Process b 2.2 g (0.008 mol) of 1-(4-cyano-2,5-difluorophenyl)-4-methyl-3-dimethylamino-1,2,4-triazolin-5-one and 0.65 g (0.008 mol) of dimethylamine hydrochloride in 80 ml of dimethyl sulphoxide are admixed with 2.2 g (0.016 mol) of potassium carbonate, and the mixture is then stirred for 20 hours at 80° C. For working up, the reaction mixture is cooled and filtered, the filtrate is concentrated in vacuo, the residue is partitioned between dichloromethane and water, the organic phase is separated off, dried over sodium sulphate and concentrated in vacuo.

0.9 g (37% of theory) of 1-(4-cyano-2-fluoro-5-dimethylamino-phenyl)-4-methyl-3-dimethylamino-1,2,4-triazolin-5-one is obtained with a melting point of 109°–110° C.

EXAMPLE 4

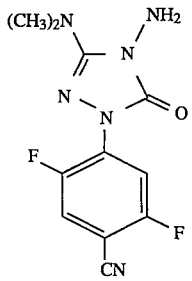

Process a 28.6 g (0.2 mol) of 3-dimethylamino-4-amino-1 H-1,2,4-triazolin-5-one (cf. e.g. EP 415 196) and 31.4 g (0.05 mol) of 2,4,5-trifluorobenzonitrile (cf. e.g. EP 191 181) in 200 ml of dimethyl sulphoxide are admixed at room temperature with 27.6 g (0.2 mol) of potassium carbonate, and the mixture is then stirred for one hour at 50° C. and a further two hours at 120° C. For working up, the reaction mixture is cooled and placed in water, the solid which is precipitated out is filtered off with suction, washed in succession with water and isopropanol and dried.

49 g (87.5% of theory) of 1-(4-cyano-2,5-difluorophenyl)-4-amino-3-dimethylamino-1,2,4-triazolin-5-one are obtained with a melting point of 154°–155° C.

EXAMPLE 5

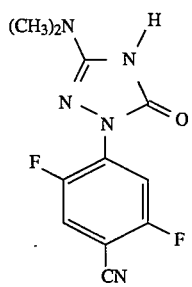

Process c

A solution of 3.5 g (0.05 mol) of sodium nitrite in 200 ml of water is added dropwise with stirring at room temperature to 14 g (0.05 mol) of 1-(4-cyano-2,5-di-fluorophenyl)-4-amino-3-dimethylamino-1,2,4-triazolin-5-one in 200 ml of acetic acid; after addition is complete, the mixture is stirred for 10 further minutes at room temperature and is then slowly heated with stirring to 80° C. For working up, the reaction mixture is cooled and filtered, the residue is washed in succession with water and ethanol and dried.

11 g (83% of theory) of 1-(4-cyano-2,5-difluorophenyl)-3-dimethylamino-4H-1,2,4-triazolin-5-one are obtained with a melting point of >250° C.

EXAMPLE 6

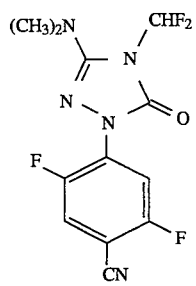

Process d 80 g (0.9 mol) of chlorodifluoromethane are passed at 0° C. to 10° C. over 5 hours into a suspension of 8.75 g (0.033 mol) of 1-(4-cyano-2,5-difluorophenyl)-3-dimethylamino-4H-1,2,4-triazolin-5-one, 3.4 g (0.06 mol) of potassium carbonate and 0.6 g of tetrabutylammmonium bromide in 200 ml of tetrahydrofuran, and after 2 hours the consumption of base is made up by adding 1.7 g (0.03 mol) of potassium hydroxide. For working up, the reaction mixture is placed in water and extracted several times with dichloromethane, the combined organic phases are dried over sodium sulphate and concentrated in vacuo, and the residue is recrystallized from isopropanol.

6.8 g (65% of theory) of 1-(4-cyano-2,5-difluorophenyl)-3-dimethylamino-4-difluoromethyl-1,2,4-triazolin-5-one are obtained with a melting point of 188°–190° C.

EXAMPLE 7

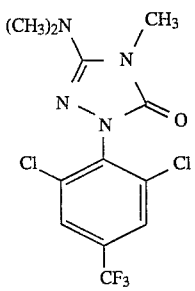

Process e/2nd Stage 8.3 g (0.05 mol) of 1-(2,6-dichloro-4-trifluoromethylphenylamino)-2,2,3-trimethylguanidinium hydrochloride in 200 ml of acetonitrile are heated slowly to reflux temperature while passing in phosgene, the evolution of hydrogen chloride commencing from about 60° C. A total of 80 g (0.8 mol) of phosgene are passed in and, when this is complete, the mixture is stirred at reflux temperature until the evolution of hydrogen chloride is at an end. For working up, the reaction mixture is cooled and concentrated in vacuo, the residue is stirred with ethyl acetate and filtered, the filtrate is concentrated again in vacuo and the residue is recrystallized from cyclohexane.

13 g (73% of theory) of 1-(2,6-dichloro-4-trifluoromethylphenyl)-3-dimethylamino-4-methyl-1,2,4-triazolin-5-one are obtained with a melting point of 105°–107° C.

PREPARATION OF THE STARTING COMPOUNDS

EXAMPLE VIII-1

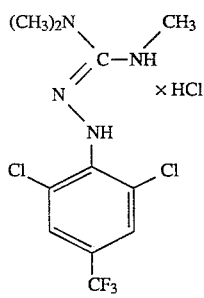

Process e/1st Stage

A solution of 15.7 g (0.1 mol) of chlorotrimethylformamidinium hydrochloride (cf. e.g. EP 283 876) in 100 ml of isopropanol is added dropwise with stirring at room temperature (not more than 30° C.) to 49 g (0.2 mol) of 2,6-dichloro-4-trifluoromethylphenylhydrazine (cf. e.g. EP 187 285) in 300 ml of isopropanol; after addition is complete, the mixture is stirred for 30 further minutes at room temperature. For working up, the reaction mixture is filtered and the filtrate is concentrated in vacuo, the residue is induced to crystallize by stirring with ethyl acetate, and the crystals are filtered off and dried.

29 g (80% of theory) of 1-(2,6-dichloro-4-trifluoromethylphenylamino)-2,2,3-trimethylguanidinium hydrochloride are obtained with a melting point of 236°–238° C.

EXAMPLE II-1

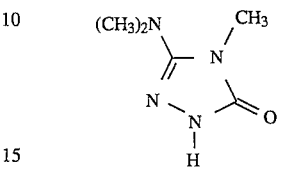

A solution of 620 g (3.95 mol) of chlorotrimethylformamidinium hydrochloride (cf. e.g. EP 283 876) in 1,600 ml of acetonitrile is added dropwise with stirring at room temperature (up to a maximum of 30° C.) to 411 g (3.95 mol) of ethyl carbazate and 996 g (11.85 mol) of sodium hydrogen carbonate in 2,000 ml of acetonitrile; after addition is complete, the mixture is heated slowly to reflux temperature and stirred for a further 10 hours at reflux temperature. For working up, the reaction mixture is cooled and filtered, the filtrate is concentrated under reduced pressure and distilled in a high vacuum.

480 g (85.5% of theory) of 3-dimethylamino-4-methyl-1H-1,2,4-triazolin-5-one are obtained with a boiling point of 178°–180° C. at 4 mbar and with a melting point of 78°–80° C.

In a corresponding manner and in accordance with the general preparation instructions, the following 1H-triazolinones of the general formula (II) are obtained:

| Ex. No. | $R^1$ | $R^2$ | X | physical properties |
|---|---|---|---|---|
| II-2 | $(CH_3)_2N-$ | $i-C_3H_7$ | O | m.p. 125–126° C. |
| II-3 | $H_3C$<br>$\phantom{XX}\diagdown$<br>$\phantom{XXXX}N-$<br>$\phantom{XX}\diagup$<br>$H_5C_2$ | $CH_3$ | O | m.p. 69–70° C. |
| II-4 | $(CH_3)_2N-$ | $C_2H_5$ | O | m.p. 58–59° C. |
| II-5 | $(C_2H_5)_2N-$ | $CH_3$ | O | m.p. 84–85° C. |
| II-6 | $O\diagup\diagdown N-$ | $CH_3$ | O | m.p. 172–173° C. |

The $^1$H-NMR spectra were recorded in deuterochloroform (CDCl$_3$) with tetramethylsilane (TMS) as the internal standard. The value given is the chemical shift δ in ppm.

EXAMPLE III-1

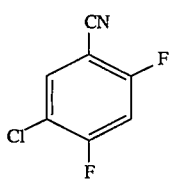

220 g (1.06 mol) of 2,4,5-trichlorobenzonitrile (cf. e.g. EP 441 004) are added at room temperature with stirring to 250 g (4.31 mol) of potassium fluoride in 400 ml of distilled tetramethylene sulphone, and the mixture is subsequently stirred for 10 hours at 195° C. to 200° C. For working up it is cooled, 500 ml of water are added and the mixture is subjected to a steam distillation. The organic fraction is taken up in dichloromethane, dried over sodium sulphate, concentrated in vacuo and distilled.

108 g (58% of theory) of 2,4-difluoro-5-chlorobenzonitrile are obtained with a boiling point of 105°–107° C. at 30 mbar and with a melting point of 48°–50° C.

In a corresponding manner and in accordance with the general preparation instructions, the following substituted triazolinones of the general formula (I) are obtained:

TABLE II

Structure (I): triazolinone bearing substituents $R^1$, $R^2$ at the azole ring and a phenyl group with $R^3$–$R^7$; X on the carbonyl.

| Ex. No. | $R^1$, $R^2$, X (triazolinone portion) | Phenyl substituents ($R^3$–$R^7$) | physical properties |
|---|---|---|---|
| 8 | $R^1 = (CH_3)_2N$; $R^2 = N=C(CH_3)(i\text{-}C_4H_9)$; X = O | 2,5-difluoro-4-CN | m.p. 133–134° C. |
| 9 | $R^1 = (CH_3)_2N$; $R^2 = NH\text{-}CO\text{-}CF_3$; X = O | 2,5-difluoro-4-CN | m.p. 165–166° C. |
| 10 | $R^1 = H_3C\text{-}NH$; $R^2 = CH_3$; X = O | 2,5-difluoro-4-CN | m.p. >250° C. |

TABLE II-continued
| Ex. No. | 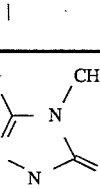 | 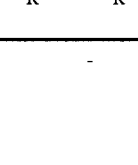 | physical properties |
|---|---|---|---|
| 11 | (CH₃)₂N, CH₃, N, N, N, S (X=S) | 2,5-difluoro-4-CN phenyl | m.p. 138° C. |
| 12 | (CH₃)₂N, CH₃, N, N, N, O | 2-O-iC₃H₇, 3-CN, 5-F phenyl | m.p. 230° C. |
| 13 | (CH₃)₂N, CH₃, N, N, N, O | 3-CN, 5-F phenyl | m.p. 110° C. |
| 14 | (CH₃)₂N, CH₃, N, N, N, O | 2-Cl, 3-F, 4-CF₃, 6-Cl phenyl | ¹H-NMR*): 2.77; 3.35; 7.67–7.69 |
| 15 | (CH₃)₂N, CH₃, N, N, N, O | 2-F, 3-CF₃, 5-F phenyl | ¹H-NMR*): 2.78; 3.35; 7.4–7.55 |
| 16 | (CH₃)₂N, CH₃, N, N, N, O | 2-Cl, 3-F, 4-CF₃ phenyl | m.p. 95–96° C. |

TABLE II-continued
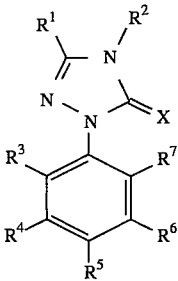
(I)
| Ex. No. | 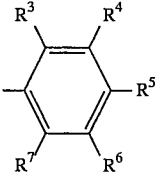 | 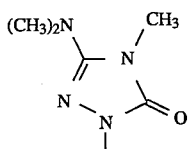 | physical properties |
|---|---|---|---|
| 17 | 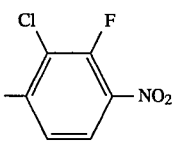 | 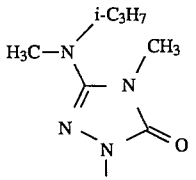 | m.p. 230° C. |
| 18 | 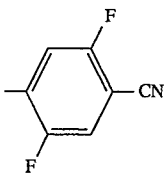 | 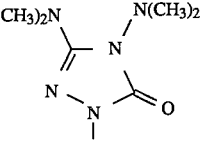 | m.p. 107–109° C. |
| 19 | 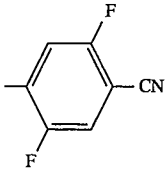 | 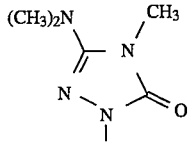 | m.p. 84–88° C. |
| 20 | 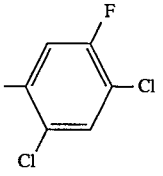 | 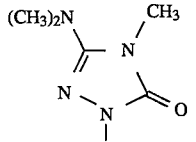 | m.p. 125–126° C. |
| 21 | 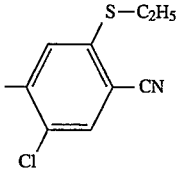 | 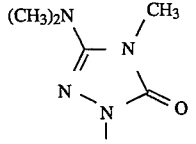 | m.p. 142–143° C. |
| 22 | 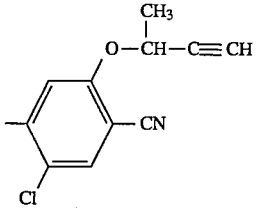 | | m.p. 147–148° C. |

TABLE II-continued
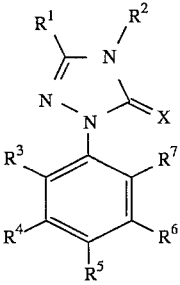
(I)
| Ex. No. | R¹R²N-triazolinone | Phenyl substituent | physical properties |
|---|---|---|---|
| 23 | (CH₃)₂N, CH₃, N-N-CH₃, X=O | O—CH₂—CH₂—S—C₂H₅; CN; F | ¹H-NMR*): 1.28; 1.35; 2.78; 4.22–4.25 |
| 24 | (CH₃)₂N, CH₃, N-N-CH₃, X=O | O—CH₂—CH=CH₂; CN; F | m.p. 122–123° C. |
| 25 | (CH₃)₂N, CH₃, N-N-CH₃, X=O | O—CH₂—CH₂—O-i-C₃H₇; CN; F | m.p. 64–65° C. |
| 26 | (CH₃)₂N, CH₃, N-N-CH₃, X=O | O—CH₂-(2-pyridyl); CN; F | m.p. 142–143° C. |
| 27 | (CH₃)₂N, CH₃, N-N-CH₃, X=O | O—CH₂-(tetrahydropyran-2-yl); CN; F | ¹H-NMR*): 2.78; 3.48–3.53; 3.72–3.78 |

TABLE II-continued

| Ex. No. | $R^1, R^2, X$ substituents (triazolinone) | $R^3$–$R^7$ substituents (phenyl) | physical properties |
|---|---|---|---|
| 28 | $R^1=(CH_3)_2N$, $R^2=CH_3$, N-CH$_3$, X=O | $NH-SO_2-CH_3$, CN | m.p. 236–237° C. |
| 29 | $R^1=(CH_3)_2N$, $R^2=CH_3$, N-CH$_3$, X=O | $S-C_2H_5$, CN, F | m.p. 123–124° C. |
| 30 | $R^1=(CH_3)_2N$, $R^2=CH_3$, N-CH$_3$, X=O | $O$-(4-F-phenyl), CN, F | m.p. 163–164° C. |
| 31 | $R^1=(CH_3)_2N$, $R^2=CH_3$, N-CH$_3$, X=O | CN, CN | m.p. 188–189° C. |
| 32 | $R^1=(CH_3)_2N$, $R^2=CH_3$, N-CH$_3$, X=O | Cl, $NH-SO_2-CH_3$, $CF_3$, Cl | m.p. >25° C. |

TABLE II-continued
| Ex. No. | 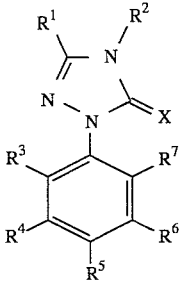 | 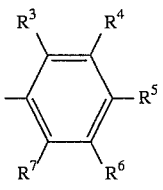 | physical properties |
|---|---|---|---|
| 33 | 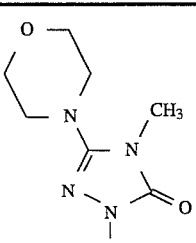 | 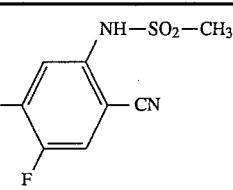 | $^1$H-NMR*): 3.12; 3.20–3.25; 3.30; 3.85–3.90 |
| 34 | 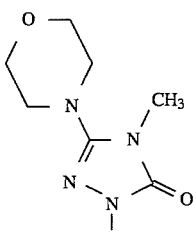 | 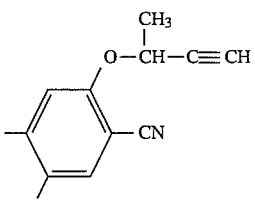 | m.p. 148–150° C. |
| 35 | 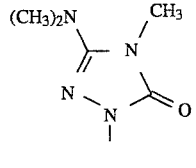 | 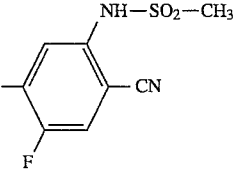 | m.p. 200–202° C. |
| 36 | 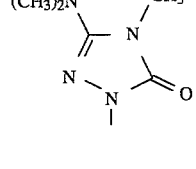 | 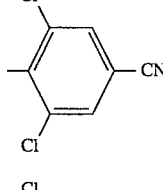 | m.p. 157–158° C. |
| 37 | 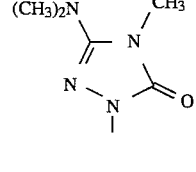 | 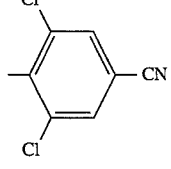 | m.p. 210–211° C. |

TABLE II-continued

Structure (I):
R¹—C(=N-R²)-N(-N=)-C(=X)- attached to phenyl with R³,R⁴,R⁵,R⁶,R⁷

| Ex. No. | [triazolone structure with R¹, R² and X] | [phenyl with R³, R⁴, R⁵, R⁶, R⁷] | physical properties |
|---|---|---|---|
| 38 | R¹=(CH₃)₂N, R²=CH₃, X=O | 2-NH(cyclohexyl), 6-CN, 4-F | m.p. 153–154° C. |
| 39 | R¹=(CH₃)₂N, R²=CH₃, X=O | 2-O-(4-Cl-3,5-dimethylphenyl), 6-CN, 4-F | m.p. 172–173° C. |
| 40 | R¹=(CH₃)₂N, R²=CH₃, X=O | 2-O-(3,4-dimethoxyphenyl), 6-CN, 4-F | m.p. 135–136° C. |
| 41 | R¹=H₃C—N(i-C₃H₇)—, R²=CH₃, X=O | 2-O-CH(CH₃)-C≡CH, 6-CN, 4-F | m.p. 250° C. |
| 42 | R¹=(CH₃)₂N, R²=CH₃, X=O | 2,6-diCl, 3-CN (2-CN, 3,6-diCl) | m.p. 157–158° C. |

TABLE II-continued
| Ex. No. | 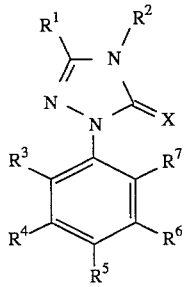 | 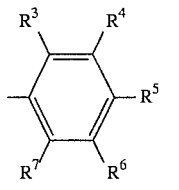 | physical properties |
|---|---|---|---|
| 43 | (CH₃)₂N, NH—CH₃ triazolinone | 2,5-difluoro-4-CN phenyl | m.p. 157–158° C. |
| 44 | (CH₃)₂N, CH₃ triazolinone | 2-CH₃, 4-NO₂ phenyl | m.p. 135–136° C. |
| 45 | (C₂H₅)₂N, CH₃ triazolinone | 2,5-difluoro-4-CN phenyl | m.p. 87–88° C. |
| 46 | (CH₃)₂N, C₂H₅ triazolinone | 2,5-difluoro-4-CN phenyl | m.p. 108–109° C. |
| 47 | (CH₃)₂N, C₂H₅ triazolinone | NH—SO₂—CH₃, CN, F phenyl | m.p. 182–183° C. |
| 48 | (C₂H₅)₂N, CH₃ triazolinone | O—CH(CH₃)—C≡CH, CN, F phenyl | m.p. 99–101° C. |

TABLE II-continued

Structure (I): triazolinone with R1, R2, X on the ring and phenyl bearing R3, R4, R5, R6, R7

| Ex. No. | Triazolinone substituents | Phenyl substituents | physical properties |
|---|---|---|---|
| 49 | R1=(CH₃)₂N, R2=CH₃, X=O, N-CH₃ | 4-NO₂ | m.p. 130–131° C. |
| 50 | R1=(CH₃)₂N, R2=N(CH₃)₂, X=O, N-CH₃ | 2-NH-SO₂-CH₃, 5-CN, 4-F | m.p. 167–168° C. |
| 51 | R1=(CH₃)₂N, R2=N(CH₃)₂, X=O, N-CH₃ | 2-O-CH(CH₃)-C≡CH, 5-CN, 4-F | m.p. 108–109° C. |
| 52 | R1=(CH₃)₂N, R2=C₂H₅, X=O, N-CH₃ | 2-O-CH(CH₃)-C≡CH, 5-CN, 4-F | m.p. 103–104° C. |
| 53 | R1=(CH₃)₂N, R2=C₂H₅, X=O, N-CH₃ | 2-NH-SO₂-CH₃, 5-CN, 4-F | m.p. 234–235° C. |

TABLE II-continued

Structure (I):
Triazole core with R¹, R², R³, R⁴, R⁵, R⁶, R⁷ substituents and X on the carbonyl, attached to a phenyl ring.

| Ex. No. | Triazole (R¹, R², X) | Phenyl substituents (R³–R⁷) | physical properties |
|---|---|---|---|
| 54 | R¹=(CH₃)₂N, R²=CH₃, X=O, N-CH₃ | HN—CH₂—C(CH₃)=CH₂; CN; F | m.p. 168–169° C. |
| 55 | R¹=(CH₃)₂N, R²=CN, X=O, N-CH₃ | F; CN; F | m.p. 151–152° C. |
| 56 | R¹=(CH₃)₂N, R²=CH₃, X=O, N-CH₃ | O—CH(CH₂—N(CH₃)₂)—CH=CH₂; CN; F | ¹H-NMR*): 2.37; 2.88; 3.30 |
| 57 | R¹=(CH₃)₂N, R²=CH₃, X=O, N-CH₃ | HN—CH(CH₃)—C₆H₅; CN; F | m.p. 191–192° C. |
| 58 | R¹=(CH₃)₂N, R²=CH₃, X=O, N-CH₃ | NH—SO₂—CH₃; CN; F | m.p. 259–261° C. |

TABLE II-continued

Formula (I): triazolinone with R¹, R² on one side and X, and phenyl ring substituted with R³–R⁷.

| Ex. No. | R¹, R² (triazolinone) | Phenyl substituents (R³–R⁷) | physical properties |
|---|---|---|---|
| 59 | (CH₃)₂N–, CH₃, X=O, N-CH₃ | O–CH(CH₃)–C≡CH; CN; F | m.p. 240–241° C. |
| 60 | H₃C–N(CH₃)–, C₂H₅/CH₃, X=O, N-CH₃ | F; CN; F | m.p. 77–78° C. |
| 61 | (CH₃)₂N–, H, X=O, N-CH₃ | NH–SO₂–CH₃; CN; F | m.p. >250° C. |
| 62 | H₃C–N(C₂H₅)–, CH₃, X=O, N-CH₃ | O–CH(CH₃)–C≡CH; CN; F | m.p. 107–108° C. |
| 63 | H₃C–N(C₂H₅)–, CH₃, X=O, N-CH₃ | NH–SO₂–CH₃; CN; F | m.p. 180–181° C. |

TABLE II-continued
| Ex. No. | 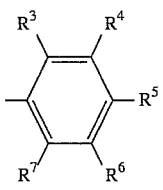 | 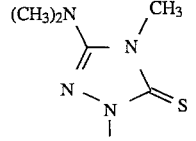 | physical properties |
|---|---|---|---|
| 64 | 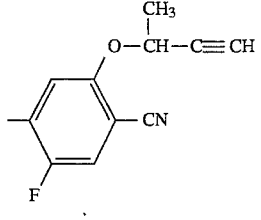 | 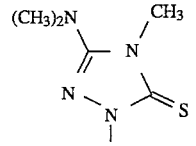 | $^1$H-NMR*): 1.75–1.78; 2.60; 2.92; 3.60 |
| 65 | 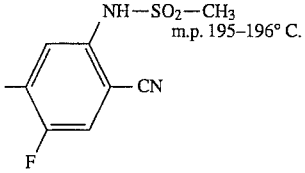 | 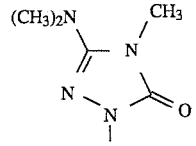 | m.p. 195–196° C. |
| 66 | 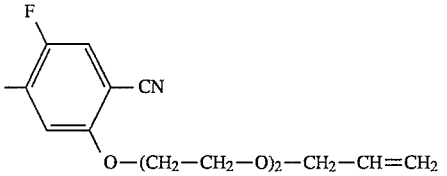 | 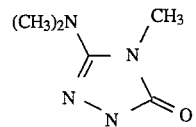 | $^1$H-NMR*): 1.21–1.25; 2.85; 5.85–5.98 |
| 67 | 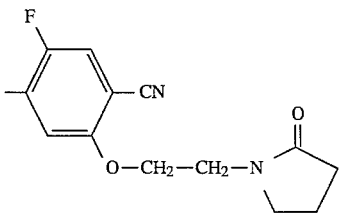 | 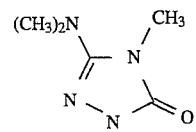 | m.p. 146–147° C. |
| 68 | 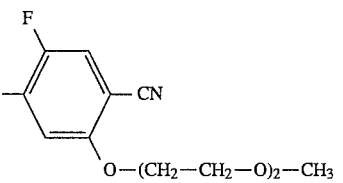 | 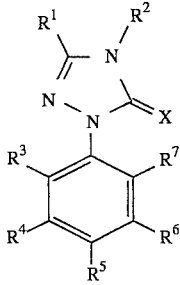 | m.p. 78–80° C. |

TABLE II-continued

| Ex. No. | $R^1$, $R^2$, X (triazolinone) | Phenyl substituents | physical properties |
|---|---|---|---|
| 69 | $R^1=(CH_3)_2N$, $R^2=CH_3$, X=O, N-CH$_3$ | 2-O-CH$_2$-CH=CH$_2$, 4-CN, 5-F | m.p. 84–85° C. |
| 70 | $R^1=(CH_3)_2N$, $R^2=CH_3$, X=O, N-CH$_3$ | 2-F, 5-CN, 4-O-(CH$_2$-CH$_2$-O)$_5$-CH$_3$ | $^1$H-NMR*): 1.22–1.26; 2.88; 4.22–4.25 |
| 71 | $R^1=(CH_3)_2N$, $R^2=CH_3$, X=O, N-CH$_3$ | 2-O-CH$_2$-CH=CH-CH$_3$, 4-CN, 5-F | m.p. 94–95° C. |
| 72 | $R^1=(CH_3)_2N$, $R^2=CH_3$, X=O, N-CH$_3$ | 2-O-CH(CH$_3$)-CH$_2$-O-CH$_3$, 4-CN, 5-F | m.p. 88–90° C. |
| 73 | $R^1=(CH_3)_2N$, $R^2=NH-CH_3$, X=O, N-CH$_3$ | 2-NH-SO$_2$-CH$_3$, 4-CN, 5-F | m.p. 171–173° C. |

TABLE II-continued
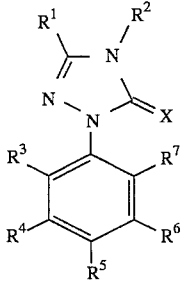
(I)
| Ex. No. | 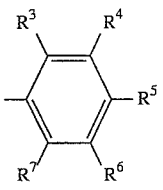 | 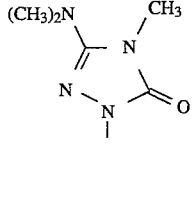 | physical properties |
|---|---|---|---|
| 74 | 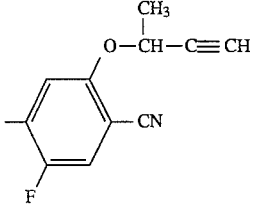 | 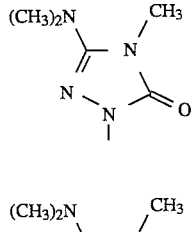 | m.p. 187–188° C. |
| 75 | 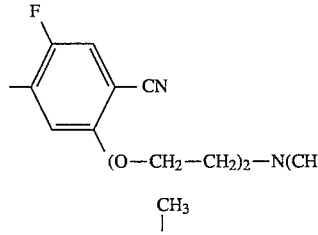 | 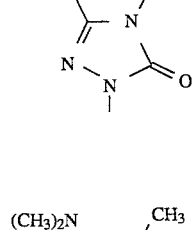 | ¹H-NMR*): 2.29; 2.90; 4.33–4.36 |
| 76 | 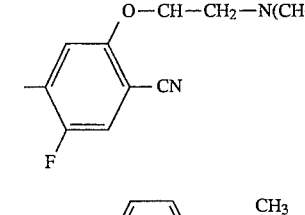 | 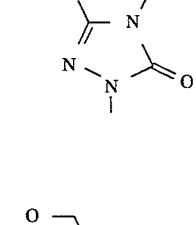 | ¹H-NMR*): 1.35–1.38; 2.33; 2.90; 4.50–4.60 |
| 77 | 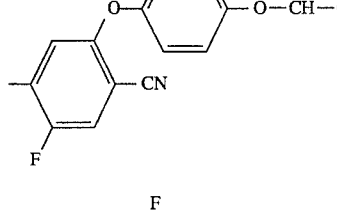 | 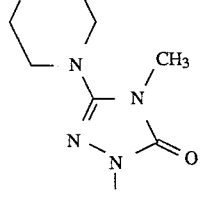 | ¹H-NMR*): 2.80; 3.25; 4.20–4.30; 4.70–4.76 |
| 78 | 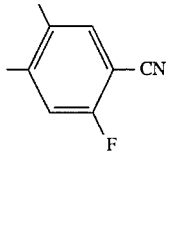 | | m.p. 164–165° C. |

TABLE II-continued (I)

| Ex. No. | [triazolinone structure with R¹, R², X] | [phenyl structure with R³–R⁷] | physical properties |
|---|---|---|---|
| 79 | R¹=(CH₃)₂N, R²=CH₃, X=O | 4-F, 2-CN, 5-NH-cyclopropyl | m.p. 214–215° C. |
| 80 | R¹=(CH₃)₂N, R²=i-C₃H₇, X=O | 4-F, 2-CN, 6-F | m.p. 123° C. |
| 81 | R¹=(CH₃)₂N, R²=i-C₃H₇, X=O | 4-F, 2-CN, 5-O-CH(CH₃)-C≡CH | m.p. 84° C. |
| 82 | R¹=(CH₃)₂N, R²=i-C₃H₇, X=O | 4-F, 2-CN, 5-NH-SO₂-CH₃ | |

*)The ¹H-NMR spectra recorded in deuterochloroform (CDCl₃) with tetramethylsilane (TMS) as the internal standard. The value given is the chemical shift δ in ppm.

APPLICATION EXAMPLES

In the following Application Example the compound listed below was employed as the comparison substance:

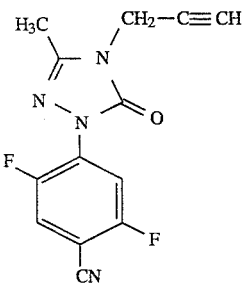

Methyl-4-propargyl-1-(2,5-difluoro-4-cyano-phenyl)-1,2,4-triazolin-5-one (known from DE 38 39 480)

EXAMPLE A

Pre-emergence Test

Solvent: 5 parts by weight of acetone

Emulsifier: 1 part by weight of alkylaryl polyglycol ether

To produce a suitable preparation of active compound, one part by weight of active compound is mixed with the stated amount of solvent, the stated amount of emulsifier is added and the concentrate is diluted with water to the desired concentration.

Seeds of the test plants are sown in normal soil and, after 24 hours, watered with the preparation of the active compound. It is expedient to keep constant the amount of water per unit area. The concentration of the active compound in the preparation is of no importance, only the amount of active compound applied per unit area being decisive. After three weeks, the degree of damage to the plants is rated in % damage in comparison to the development of the untreated control.

The figures denote:

0%=no action (like untreated control)

100%=total destruction

In this test, the compounds according to Preparation Examples 1 and 2 exhibit a marked superiority in relation to the prior art.

It will be understood that the specification and examples are illustrative but not limitative of the present invention and that other embodiments within the spirit and scope of the invention will suggest themselves to those skilled in the art.

What is claimed is:

1. A 1-aryltriazolin(ethi)one of the formula

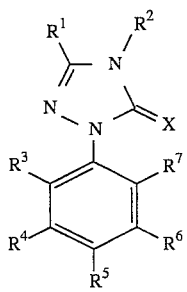

wherein $R^1$ represents a radical $-NR^8R^9$, $R^2$ represents hydrogen, amino or cyano, or represents one of the radical $-R^{10}$, $-O-R^{10}$, $-S-R^{10}$, $-NR^{10}R^{11}$, $-N(R^{11})-CO-R^{10}$ or $-N=CR^{10}R^{11}$, $R^3$, $R^6$ and $R^7$ independently of one another each represent hydrogen, fluorine, chlorine, bromine, iodine or nitro, $R^4$ represents hydrogen, fluorine, chlorine, bromine, iodine, cyano or nitro, or represents one of the radicals $-R^2$, $-O-R^{12}$, $-S-R^{12}$, $-S(O)-R^{12}$, $-SO_2-OR^{12}$, $-CO-OR^{12}$, $-CO-NR^{11}R^{12}$, $-O-SO_2-R^{12}$, $-N(R^{11})-SO_2-R^{12}$, $-NR^{11}-R^{12}$, $-NH-P(O)(R^{11})(OR^{12})$ or $-NH-P(O)(OR^{11})(OR^{12})$, $R^5$ represents nitro, cyano, fluorine, chlorine, bromine, iodine, or represents straight-chain or branched halogenoalkyl having 1 to 6 carbon atoms and 1 to 13 identical or different halogen atoms, and X represents oxygen and sulphur, $R^8$ is hydrogen when $R^9$ represents optionally substituted straight-chain or branched $C_1-C_{14}$ alkyl or alkoxy wherein the substituents are halogen; cyano; carboxyl; carbamoyl; $C_1-C_8$ straight-chain or branched alkoxy, alkoxyalkoxy, alkylthio, alkylsulphinyl, alkylsulphonyl, alkoxycarbonyl, N-alkylaminocarbonyl, N,N-dialkylaminocarbonyl or alkylsulphonylaminocarbonyl; $C_1C_6$ alkoxy, alkylthio, alkylsulphinyl or alkylsulphonyl; $C_1-C_6$ straight-chain or branched halogenoalkyl, halogenoalkoxy, halogenoalkylthio, halogenoalkylsulphinyl or halogenoalkylsulphonyl; $C_1-C_6$ straight-chain or branched alkoxycarbonyl or alkoximinoalkyl; and phenyl which is optionally substituted once or more than once by identical or different substituents selected from the group consisting of halogen, $C_1-C_6$ straight-chain or branched alkyl, $C_1-C_6$ straight-chain or branched alkoxy, $C_1-C_6$ straight-chain or branched halogenoalkyl, and $C_1-C_6$ halogenoalkoxy;

or $R^8$ and $R^9$ independently of one another represent optionally substituted straight-chain or branched $C_1-C_{14}$ alkyl or alkoxy wherein the substituents are halogen; cyano; carboxyl; carbamoyl; $C_1-C_8$ straight-chain or branched alkoxy, alkoxyalkoxy, alkylthio, alkylsulphinyl, alkylsulphonyl, alkoxycarbonyl, N-alkylaminocarbonyl, N,N-dialkylaminocarbonyl or alkylsulphonylaminocarbonyl; $C_1$–$C_6$alkoxy, alkylthio, alkylsulphinyl or alkylsulphonyl; $C_1$–$C_6$ straight-chain or branched halogenoalkyl, halogenoalkoxy, halogenoalkylthio, halogenoalkylsulphinyl or halogenoalkylsulphonyl; $C_1$–$C_6$ straight-chain or branched alkoxycarbonyl or alkoximinoalkyl; and phenyl which is optionally substituted once or more than once by identical or different substituents selected from the group consisting of halogen, $C_1$–$C_6$ straight-chain or branched alkyl, $C_1$–$C_6$ straight-chain or branched alkoxy, $C_1$–$C_6$ straight-chain or branched halogenoalkyl, and $C_1$–$C_6$ halogenoalkoxy;

$R^{10}$ represents $C_1$–$C_{14}$ straight-chain or branched alkyl which is optionally substituted once or more than once by identical or different substituents wherein the substituents are halogen; cyano; carboxyl; carbamoyl; or $C_1$–$C_8$ straight-chain or branched alkoxy, alkoxyalkoxy, alkylthio, alkylsulphinyl, alkylsulphonyl, alkoxycarbonyl, N-alkylaminocarbonyl, N,N-dialkylaminocarbonyl or alkylsulphonylaminocarbonyl the individual alkyl moieties;

$R^{10}$ furthermore represents $C_2$–$C_8$ alkenyl or alkinyl which are optionally substituted once or more than once by identical or different halogens;

$R^{10}$ furthermore represents $C_3$–$C_7$ cycloalkyl which is optionally substituted once or more than once by identical or different substituents selected from the group consisting of halogen straight-chain or branched alkyl having 1 to 4 carbon atoms;

$R^{10}$ furthermore represents arylalkyl or aryl having 6 to 10 carbon atoms in the aryl moiety and optionally 1 to 4 carbon atoms in the straight chain or branched alkyl moiety, which are in each case optionally substituted in the aryl moiety once or more than once by identical or different substituents, wherein the substituents are halogen; cyano; nitro; amino; N-acetylamino; $C_1$–$C_6$ straight-chain or branched alkyl, alkoxy, alkylthio, alkylsulphinyl or alkylsulphonyl; $C_1$–$C_6$ straight-chain or branched halogenoalkyl, halogenoalkoxy, halogenoalkylthio, halogenoalkylsulphinyl or halogenoalkylsulphonyl and 1 to 13 identical or different halogen atoms; $C_1$–$C_6$ straight-chain or branched alkoxycarbonyl or alkoxyiminoalkyl; and phenyl which is optionally substituted once or more than once by identical or different substituents selected from the group consisting of halogen, $C_1$–$C_6$ straight-chain or branched alkyl, $C_1$–$C_6$ straight-chain or branched alkoxy, $C_1$–$C_6$ straight-chain or branched halogenoalkyl and $C_1$–$C_6$ straight-chain or branched halogenoalkoxy;

$R^{11}$ represents hydrogen;

$R^{11}$ furthermore represents straight-chain or branched alkyl having 1 to 14 carbon atoms which is optionally substituted once or more than once by identical or different substituents wherein the substituents are halogen; cyano; carboxyl; carbamoyl; $C_1$–$C_8$ straight-chain or branched alkoxy, alkoxyalkoxy, alkylthio, alkylsulphinyl, alkylsulphonyl, alkoxycarbonyl, N-alkylaminocarbonyl, N,N-dialkylaminocarbonyl or alkylsulphonylaminocarbonyl;

$R^{11}$ furthermore represents alkenyl or alkinyl having in each case 2 to 8 carbon atoms, which are optionally substituted once or more than once by identical or different halogens;

$R^{11}$ furthermore represents cycloalkyl having 3 to 7 carbon atoms which is optionally substituted once or more than once by identical or different substituents selected from the group consisting of halogen and straight-chain or branched alkyl having 1 to 4 carbon atoms;

$R^{11}$ furthermore represents arylalkyl or aryl having in each case 6 to 10 carbon atoms in the aryl moiety and optionally 1 to 4 carbon atoms in the straight-chain or branched alkyl moiety, wherein the aryl moiety is optionally substituted once or more than once by identical or different substituents, wherein the substituents are halogen; cyano; nitro; amino; N-acetylamino; $C_1$–$C_6$ alkoxy, alkylthio, alkylsulphinyl or alkylsulphonyl; $C_1$–$C_6$ straight-chain or branched halogenoalkyl, halogenoalkoxy, halogenoalkylthio, halogenoalkylsulphinyl or halogenoalkylsulphonyl; $C_1$–$C_6$ straight-chain or branched alkoxycarbonyl or alkoximinoalkyl; and phenyl which is optionally substituted once or more than once by identical or different substituents selected from the group consisting of halogen, $C_1$–$C_6$ straight-chain or branched alkyl, $C_1$–$C_6$ straight-chain or branched alkoxy, $C_1$–$C_6$ straight-chain or branched halogenoalkyl, and $C_1$–$C_6$ straight-chain or branched halogenoalkoxy;

$R^{12}$ represents hydrogen;

$R^{12}$ furthermore represents straight-chain or branched alkyl having 1 to 14 carbon atoms which is optionally substituted once or more than once by identical or different substituents wherein the substituents are halogen; cyano; carboxyl; carbamoyl; $C_1$–$C_8$ straight-chain or branched alkoxy, alkoxyalkoxy, alkylthio, alkylsulphinyl, alkylsulphonyl, alkoxycarbonyl, N-alkylaminocarbonyl, N,N-dialkylaminocarbonyl or alkylsulphonylaminocarbonyl;

$R^{12}$ furthermore represents alkenyl or alkinyl having in each case 2 to 8 carbon atoms, which are in each case optionally substituted once or more than once by identical or different halogens;

$R^{12}$ furthermore represents cycloalkyl having 3 to 7 carbon atoms which is optionally substituted once or more than once by identical or different substituents selected from the group consisting of halogen, straight-chain or branched alkyl having 1 to 4 carbon atoms;

$R^{12}$ furthermore represents arylalkyl or aryl having 6 to 10 carbon atoms in the aryl moiety and optionally 1 to 4 carbon atoms in the straight-chain or branched alkyl moiety, wherein the aryl moiety is optionally substituted once or more than once by identical or different substituents, wherein the substituents are halogen; cyano; nitro; amino; N-acetylamino; $C_1$–$C_6$ straight-chain or branched alkyl, alkoxy, alkylthio, alkylsulphinyl or alkylsulphonyl; $C_1$–$C_6$ straight-chain or branched halogenoalkyl, halogenoalkoxy, halogenoalkylthio, halogenoalkylsulphinyl or halogenoalkylsulphonyl; $C_1$–$C_6$ straight-chain or branched alkoxycarbonyl or alkoximinoalkyl; and phenyl which is optionally substituted once or more than once by identical or different substituents selected from the group consisting of halogen, $C_1$–$C_6$ straight-chain or branched alkyl, $C_1$–$C_6$ straight-chain or branched alkoxy; $C_1$–$C_6$ straight-chain or branched halogenoalkyl and $C_1$–$C_6$ straight-chain or branched and $C_1$–$C_6$ straight-chain or branched halogenoalkoxy.

2. A compound according to claim 1 of the formula

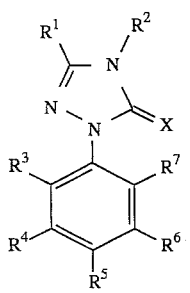

(Ia)

wherein $R^4$ represents halogen.

3. A compound according to claim 1 of the formula

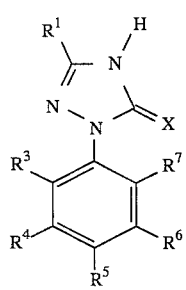

(Ic)

4. A herbicidal composition comprising a herbicidally effective amount of a compound according to claim 1 and a diluent.

5. A method of combating unwanted vegetation which comprises applying to such vegetation or to a locus from which it is desired to exclude such vegetation a herbicidally effective amount of a compound according to claim 1.

6. A compound according to claim 1 wherein such compound is 1-(4-cyano-2,5-difluorophenyl)-4-methyl-3 -dimethylamino-1,2,4-triazolin-5-one of the formula

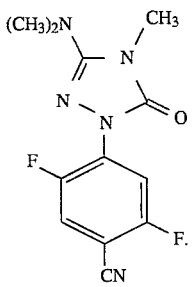

7. A compound according to claim 1 wherein such compound is 1-(4-cyano-2-fluoro-5-but-1-in-3-yl-oxy-phenyl)-4 -methyl-3-dimethylamino-1,2,4-triazolin-5-one of the formula

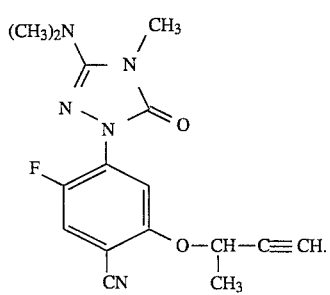

8. The method according to claim 5 wherein such compound is 1-(4-cyano-2,5-difluorophenyl)-4-methyl-3 -dimethylamino-1,2,4-triazolin-5-one;

1-(4-cyano-2-fluoro-5-but-1-in-3-yl-oxy-phenyl)-4 -methyl-3-dimethylamino-1,2,4-triazolin-5-one.

* * * * *

UNITED STATES PATENT AND TRADEMARK OFFICE
CERTIFICATE OF CORRECTION

PATENT NO.   : 5,476,946
DATED        : December 19, 1995
INVENTOR(S)  : Linker, et al.

It is certified that error appears in the above-indentified patent and that said Letters Patent is hereby corrected as shown below:

Col. 106, line 27   Delete " $-R^2$, " and substitute -- $-R^{12}$, --

Signed and Sealed this

Second Day of July, 1996

Attest:

BRUCE LEHMAN

Attesting Officer    Commissioner of Patents and Trademarks